(12) United States Patent
Kolczewski et al.

(10) Patent No.: US 8,399,674 B2
(45) Date of Patent: Mar. 19, 2013

(54) QUINOLINES

(75) Inventors: Sabine Kolczewski, Loerrach (DE); Claus Riemer, Freiburg (DE); Lucinda Steward, Basel (CH); Juergen Wichmann, Steinen (DE); Thomas Woltering, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 13/359,933

(22) Filed: Jan. 27, 2012

(65) Prior Publication Data

US 2012/0136018 A1    May 31, 2012

Related U.S. Application Data

(63) Continuation of application No. 12/233,625, filed on Sep. 19, 2008, now abandoned.

(30) Foreign Application Priority Data

Sep. 27, 2007 (EP) .................................. 07117420

(51) Int. Cl.
C07D 215/38    (2006.01)
(52) U.S. Cl. ........................ 546/163; 546/159
(58) Field of Classification Search .............. 546/159, 546/163; 514/313
See application file for complete search history.

(56) References Cited

U.S. PATENT DOCUMENTS

| | | | | |
|---|---|---|---|---|
| 6,897,220 B2 * | 5/2005 | Delorme et al. | .............. | 514/275 |
| 2007/0299074 A1 | 12/2007 | Netz et al. | | |
| 2009/0227570 A1 * | 9/2009 | Kolczewski et al. | ........ | 514/228.2 |
| 2009/0227583 A1 * | 9/2009 | Kolczewski et al. | ........ | 514/235.2 |
| 2009/0233927 A1 * | 9/2009 | Kolczewski et al. | ........ | 514/235.2 |

FOREIGN PATENT DOCUMENTS

| | | |
|---|---|---|
| WO | 02/24682 | 3/2002 |
| WO | 03/024448 | 3/2003 |
| WO | 03/045313 | 6/2003 |
| WO | 2004/080463 | 9/2004 |
| WO | 2004/096771 | 11/2004 |
| WO | 2005/037285 | 4/2005 |
| WO | 2005/082871 | 9/2005 |
| WO | 2006/117305 | 11/2006 |
| WO | 2007/000392 | 1/2007 |
| WO | 2007/000393 | 1/2007 |
| WO | 2007/022946 | 3/2007 |
| WO | 2008/037626 | 4/2008 |

OTHER PUBLICATIONS

Dubertret et al., "J. of Psychiatric Research" 35:371-376 ( 2004).
Doly et al., "The Journal of Comparative Neurology" 476:316-329 ( 2004).
Sprouse et al., "Synapse" 54(2):111-118 ( 2004).
Garcia-Ladona et al., "36th Annual Meeting Soc. Neurosci. Oct. 14-18" (Atlanta Abstract 33.1), ( 2006).
Francken et al., "Eur. J. Pharmacol." 361:299-309 ( 1998).
Barnes et al., "Neuropharmacology" 38:1083-1152 ( 1999).
Drescher et al., "36th Annual Meeting Soc. Neurosci. Oct. 14-18" (Atlanta Abstract 33.2), ( 2006).
Wang et al., "Neurosci. Lett." 278:9-12 ( 2000).
Rees et al., "FEBS Lett." 355:242-246 ( 1994).
Thomas, D. R., Pharmacol. Ther., 111(3):707-714 ( 2006).
Hoyer et al., "Pharmacol. Rev." 46:157-204 ( 1994).
Pasqualetti et al., "Mol. Brain Res." 56:1-8 ( 1998).
Birkett et al., "Neuroreport" 11:2017-2020 ( 2000).
Iwata et al., "Mol. Psychiatry" 6:217-219 ( 2001).
Noda et al., "J. Neurochem." 84:222-232 ( 2003).
Duncan et al., "Brain Research" 869:178-185 ( 2000).
Thomas et al., "Neuropharmacology" 51(3):566-577 ( 2006).
(Translation of Jap Off Act in Corres Jap Appl 2010526250 Oct. 30,2012).

* cited by examiner

*Primary Examiner* — D M Seaman
(74) *Attorney, Agent, or Firm* — George W. Johnston; Patricia S. Rocha-Tramaloni; Kimberly J. Prior

(57) ABSTRACT

The present invention relates to 2-aminoquinolines of formula I

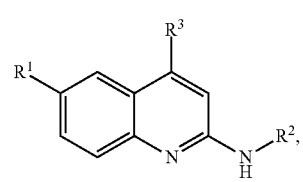

wherein $R^1$, $R^2$ and $R^3$ are as defined in the specification, as 5-HT$_{5A}$ receptor antagonists, their manufacture, pharmaceutical compositions containing them and their use for the treatment of CNS disorders.

17 Claims, No Drawings

QUINOLINES

PRIORITY TO RELATED APPLICATIONS

This application is a continuation of U.S. application Ser. No. 12/233,625, filed Sep. 19, 2008, now pending; which claims the benefit of European Patent Application 07117420.5, filed Sep. 27, 2007. The entire contents of the above-identified applications are hereby incorporated by reference.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., Pharmacol. Rev. 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT3) and the G-protein-coupled 7-transmembrane receptors (thirteen distinct receptors cloned to date). In addition, within the G-protein-coupled receptors, serotonin exerts its actions through an array of signal transduction mechanisms.

The $5\text{-HT}_{5A}$ receptor is one of 13 G-protein coupled 5-HT receptors and is Gi-α-coupled, inhibiting adenylate cyclase. The receptor protein DNA sequence is not closely related to that of any previously known serotonin receptor, with the best homology being 35% to the human $5\text{-HT}_{1B}$ receptor. It encodes a predicted 357 amino-acid protein, with seven putative transmembrane domains, consistent with that of a G-protein coupled receptor. The sequence is characterized by containing an intron between transmembrane domains V and VI ($5\text{-HT}_{5A}$; Barnes, N. M., & Sharp, T. (1999). A review of central 5-HT receptors and their function. Neuropharmacology 38, 1083-1152; Thomas D. R. $5\text{-HT}_{5A}$ receptors as a therapeutic target. Pharmacol Ther. (2006), 111(3):707-14; Francken B. J., Jurzak M., Vanhauwe J. F., Luyten W. H., Leysen J. E. The human $5\text{-HT}_{5A}$ receptor couples to Gi/Go proteins and inhibits adenylate cyclase in HEK 293 cells. Eur. J. Pharmacol. (1998), 361(2-3):299-309. A recent review by Thomas (Pharmacology & Therapeutics, 111, 707-714; 2006) describes the potential therapeutic utility of $5\text{-HT}_{5A}$ receptor ligands for the treatment of circadian rhythm, sleep disturbances, mood disorders, schizophrenia, cognitive disorders and autism.

The human $5\text{-HT}_{5A}$ mRNA is distributed in CNS areas, such as the thalamus, limbic cortex, ventrolateral amygdala, hippocampus, and hypothalamus (Pasqualetti, M., Ori, M., Nardi, I., Castagna, M., Cassano, G. B., & Marazziti, D. (1998). Distribution of the $5\text{-HT}_{5A}$ serotonin receptor mRNA in the human brain. Mol Brain Res 56, 1-8). All of these CNS areas are implicated in either the pathology or treatment of schizophrenia and anxiety. The receptor has not been detected in peripheral organs (Rees, S., Dendaas, I., Foord, S., Goodson, S., Bull, D., Kilpatrick, G., et al. (1994). Cloning and characterisation of the human $5\text{-HT}_{5A}$ serotonin receptor. FEBS Lett 355, 242-246), although it is expressed in rat superior cervical ganglia (Wang, Z. Y., Keith, I. M., Beckman, M. J., Brownfield, M. S., Vidruk, E. H. and Bisgard, G. E. (2000) $5\text{-HT}_{5A}$ receptors in the carotid body chemoreception pathway of rat. Neurosci. Lett. 278, 9-12) and the spinal cord dorsal horn which may indicate the involvement of the $5\text{-HT}_{5A}$ receptor in central motor control, nociception and autonomic function such as stress induced urinary incontinence and overactive bladder (Doly, S., Fischer, J., Brisorgueil, M.-J., Verge, D. and Conrath M. $5\text{-HT}_{5A}$ Receptor Localization in the Rat Spinal Cord Suggests a Role in Nociception and Control of Pelvic Floor Musculature The Journal of comparative neurology 476:316-329 (2004)). Gene association studies investigating the occurrence of several common polymorphisms within the $5\text{-HT}_{5A}$ receptor gene, such as—19G/C which shows allelic association with bipolar affective disorder, unipolar depression and schizophrenia (Birkett, J. T., Arranz, M. J., Munro, J., Osbourn, S., Kerwin, R. W., Collier, D. A., 2000. Association analysis of the $5\text{-HT}_{5A}$ gene in depression, psychosis and antipsychotic response. Neuroreport 11, 2017-2020). In addition, an allelic association of the polymorphism Pro-15-Ser was found within a large proportion of Japanese schizophrenic patients (Iwata, N., Ozaki, N., Inada, T., & Goldman, D. (2001). Association of a $5\text{-HT}_{5A}$ receptor polymorphism, Pro15Ser, to schizophrenia. Mol Psychiatry 6, 217-219).

Until recently, pharmacological characterisation of the $5\text{-HT}_{5A}$ receptor has been limited due to lack of available selective ligands. However, in 2006 Garcia-Ladona, F. J. et al. 36th Annu. Meet. Soc. Neurosci. (2006), October 14-18, Atlanta, Abstract 33.1 (see also WO 2005082871) reported preclinical evidence that certain selective $5\text{-HT}_{5A}$ receptor antagonists have an antipsychotic profile in animal models of schizophrenia by antagonizing methamphetamine and MK-801-induced hyperlocomotion, apomorphine-induced climbing and mescaline-induced scratching, while reversing disrupted social interaction (Jongen-Relo et al., 2006). Supporting evidence included, a reduction in the number of spontaneously active midbrain dopaminergic neurons observed after subchronic A-763079 treatment, suggesting potential antipsychotic-like activity. Data indicating that their $5\text{-HT}_{5A}$ receptor antagonists increase ACh levels in mPFC (Drescher, K. U. et al. 36th Annu. Meet. Soc. Neurosci. (2006), October 14-18, Atlanta, Abstr. 33.2), and suggesting the potential efficacy of $5\text{-HT}_{5A}$ receptor antagonists against the cognitive deficits associated with different psychiatric disorders, in particular schizophrenia and psychosis were also presented. Thomas et al. (2006), (SB-699551-A (3-cyclopentyl-N-[2-(dimethylamino)ethyl]-N-[(40-{[(2 phenylethypamino]methyl}-4 biphenylyl)methyl]propanamide dihydrochloride), a novel 5-ht5A receptor-selective antagonist, enhances 5-HT neuronal function: Evidence for an autoreceptor role for the 5-ht5A receptor in guinea pig brain. Neuropharmacology. 2006 September; 51(3):566-77) recently published microdialysis data demonstrating $5\text{-HT}_{5A}$ receptor antagonism of 5-CT-induced guinea-pig raphé neuronal firing and implying that the receptor may also act as an autoreceptor, with similar effects of those produced by anxiolytics and antidepressants. No behavioural data has been provided mainly due to species limitations. Furthermore, $5\text{-HT}_{5A}$ receptor is expressed in the hamster suprachiasmatic nucleus a region known to be involved in circadian timing circuitry (Duncan, M. J., Jennes, L., Jefferson, J. B., Brownfield, M. S. (2000). Localization of serotonin5A receptors in discrete regions of the circadian timing system in the Syrian hamster. Brain Research 869, 178-185). Activation of both $5\text{-HT}_{5A}$ and $5\text{-HT}_7$ receptors can produce phase advances of the circadian clock in-vitro (Sprouse J, Reynolds L, Braselton J, Schmidt A. Serotonin-induced phase advances of SCN neuronal firing in vitro: a possible role for 5-HT5A receptors? Synapse 2004 November; 54(2):111-8).

SUMMARY OF THE INVENTION

The present invention provides 2-aminoquinolines as 5-HT$_{5A}$ receptor antagonists, their manufacture, pharmaceutical compositions containing them and their use as medicaments.

In particular, the present invention provides compounds of formula (I)

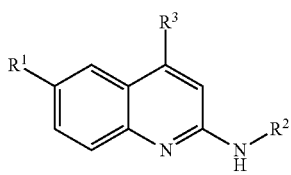

I wherein
R$^1$ is —NR$^a$—Ar$^1$, —NR$^b$CH$_2$—Ar$^1$, —CH$_2$NR$^b$—Ar$^1$, —NR$^c$C(O)—Ar$^1$, —OCH$_2$—Ar$^1$, —CH$_2$O—Ar$^1$, —CH$_2$CH$_2$—Ar$^1$, —CH=CH—Ar$^1$, —NHC(O)NH—Ar$^1$, —NHSO$_2$NH—Ar$^1$, —NR$^c$C(O)O—Ar$^1$, —C(O)NR$^c$CH$_2$—Ar$^1$, —CH$_2$NR$^b$CH$_2$—Ar$^1$, —NHC(=N—Ar$^1$)—Ar$^1$, —NR$^b$CH$_2$CH$_2$—Ar$^1$, or —NR$^b$CH$_2$CH$_2$O—Ar$^1$, R$^2$ is —Ar$^2$, —CHR$^d$—Ar$^2$, or —CH$_2$CH$_2$O—Ar$^2$, R$^3$ is hydrogen,
  phenyl, or pyridinyl, optionally substituted with one or more C$_{1-4}$-alkyl, halo, or C$_{1-4}$-alkoxy,
  —NR$^e$R$^f$, wherein R$^e$ and R$^f$ are each independently hydrogen, or
  —(CH$_2$)$_m$—OR$^g$, wherein m is from 2 to 6, Ar$^1$ and Ar$^2$ are each independently aryl or heteroaryl, each optionally substituted by one or more B, B is C$_{1-7}$-alkoxy,
  C$_{1-7}$-haloalkoxy,
  hydroxy,
  halo,
  C$_{1-7}$-alkyl, optionally substituted with one or more halo, hydroxy, or cyano,
  —S(O)$_2$—C$_{1-7}$-alkyl,
  —NR$^i$R$^{ii}$,
  —NR$^{iii}$S(O)$_2$R$^{iv}$,
  —NR$^{iii}$C(O)R$^{iv}$,
  —C(O)NR$^{iii}$R$^{iv}$,
  —S(O)$_2$—NRiiiR$^{iv}$,
  —CH$_2$—O—R$^v$,
  —(OCH$_2$CH$_2$)$_n$—OR$^v$, wherein n is from 1 to 3,
  —CH$_2$—(OCH$_2$CH$_2$)$_n$—OR$^v$, wherein n is from 1 to 3,
  —C(O)R$^v$,
  cyano,
  nitro,
  allyl,
  C$_{3-7}$-cycloalkyl,
  5- to 7-membered monocyclic heterocycloalkyl, or
  two residues B in ortho-position to each other form a 3- to 4-membered bridge of the formula —CH$_2$CH$_2$CH$_2$—, —CH$_2$CH$_2$CH$_2$CH$_2$—, —O—C(R$^{vi}$)$_2$—O—, —OCH$_2$CH$_2$O—, or —OCH(R$^{vii}$)CH(R$^{viii}$)—, R$^a$, R$^b$, R$^c$, R$^d$, and R$^g$, are each independently hydrogen or C$_{1-7}$-alkyl;

R$^i$, R$^{ii}$, R$^{iii}$, R$^{iv}$, and R$^v$ are each independently hydrogen, C$_{1-7}$-alkyl or —(CH$_2$)$_n$—C$_{3-7}$-cycloalkyl, wherein n is from 0 to 3;

R$^{vi}$, R$^{vii}$, and R$^{viii}$, are each independently hydrogen, C$_{1-4}$-alkyl or halogen;

or a pharmaceutically acceptable salt thereof.

The compounds of formula I can contain some asymmetric carbon atoms. Accordingly, the present invention includes all stereoisomeric forms of the compounds of formula I, including each of the individual enantiomers and mixtures thereof, i.e. their individual optical isomers and mixtures thereof.

The compounds of formula I have a good affinity to the 5-HT$_{5A}$ receptor.

Compounds with 5-HT$_{5A}$ affinity can be used for the manufacture of medicaments for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders, psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome.

The preferred indications with regard to the present invention are the treatment of anxiety, depression, sleep disorders and schizophrenia.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1-4 carbon atoms.

The term "halo" or "halogen" denotes fluorine, chlorine, bromine and iodine.

The alkyl or C$_{1-7}$-alkyl group as defined above can optionally be substituted with one or more halo, hydroxy or cyano, alternatively also referred to as "halo-C$_{1-7}$-alkyl", "hydroxy-C$_{1-7}$-alkyl", or "cyano-C$_{1-7}$-alkyl". Thereby, at least one of the hydrogen atoms of the alkyl group is replaced by a halogen atom, a hydroxy group or a cyano group.

The term "halo-C$_{1-7}$-alkyl" hence denotes a C$_{1-7}$-alkyl group as defined above wherein at least one of the hydrogen atoms of the alkyl group is replaced by a halogen atom, preferably fluoro or chloro, most preferably fluoro. Examples of halo-$C_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-7}$-alkyl groups are difluoro- or trifluoro-methyl or -ethyl.

The term "hydroxy-$C_{1-7}$-alkyl" hence denotes a $C_{1-7}$-alkyl group as defined above wherein at least one of the hydrogen atoms of the alkyl group is replaced by a hydroxy group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more hydroxy groups, preferably one hydroxy group, as well as those groups specifically illustrated by the examples herein below.

The term "cyano-$C_{1-7}$-alkyl" hence denotes a $C_{1-7}$-alkyl group as defined above wherein at least one of the hydrogen atoms of the alkyl group is replaced by a cyano group. Examples of cyano-$C_{1-7}$-alkyl include but are not limited to methyl, ethyl, propyl, isopropyl, isobutyl, sec-butyl, tert-butyl, pentyl or n-hexyl substituted by one or more cyano groups, preferably one cyano group, as well as those groups specifically illustrated by the examples herein below.

The term "alkoxy" denotes a group having an alkyl residue as defined above, which is attached via an oxygen atom, i.e. a group R'—O— wherein R' is alkyl as defined above.

The term "$C_1$-$C_7$ haloalkoxy" denotes an alkoxy group as defined above which is substituted by one or more halogen. Examples of $C_1$-$C_7$ haloalkoxy include but are not limited to methoxy or ethoxy, substituted by one or more Cl, F, Br or I atom(s) as well as those groups specifically illustrated by the examples herein below. Preferred $C_1$-$C_7$ haloalkoxy are difluoro- or trifluoro-methoxy or ethoxy.

The term "aryl" denotes a monovalent cyclic aromatic hydrocarbon moiety consisting of a mono- or bicyclic aromatic ring, for example phenyl or naphthyl. Aryl is optionally substituted as described herein.

The term "heteroaryl" denotes an aromatic monocyclic or bicyclic ring containing one, two, three or four heteroatoms selected from N, O, and S, the remaining ring atoms being C. Preferably, the monocyclic heteroaryl ring is 5 or 6 membered and the bicylcic heteroaryl ring is 9 or 10 membered. The one, two, three or four heteroatoms of the bicyclic heteroaryl moiety are located in either one or both rings. Examples for 5- or 6-membered monocyclic heteroaryl include but are not limited to pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, or tetrazolyl. Examples for 9- or 10-membered bicyclic heteroaryl include but are not limited to indolyl, benzofuranyl, benzothiophenyl, benzimidazolyl, benzoxyzolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phtalazinyl, or pteridinyl. Preferred examples for 5- or 6-membered monocyclic heteroaryl are tetrazolyl, [1,3,4]-oxadiazolyl, [1,2,4]-oxadiazolyl, imidazolyl, oxazolyl, isoxazolyl, furanyl, pyridinyl, or pyrimidinyl. A preferred example for a 9-membered bicyclic heteroaryl is benzoxazolyl. Heteroaryl is optionally substituted as described herein.

The term "aromatic" in the above sense means the presence of an electron sextet in the ring, according to Hackers rule.

The term "heterocycloalkyl" refers to a monovalent 5 to 7 membered saturated monocyclic ring containing one or two heteroatoms selected from N, O and S. Examples for heterocycloalkyl moieties are tetrahydrofuranyl, tetrahydropyranyl, pyrrolidinyl, morpholinyl, thiomorpholinyl, dioxothiomorpholinyl, piperidinyl, piperidin-2-one, piperazinyl and piperazin-2-one. A preferred heterocycloalkyl moiety is piperidinyl.

The term "cycloalkyl" refers to a monovalent carbocyclic radical of 3 to 7 carbon atoms, such as cyclopropyl, cyclopentyl, cyclohexyl or cycloheptyl. Preferred is cyclopropyl.

The term "one or more" as used herein to describe the number of optional substituents means that so many optional substituents are possible, as hydrogen atoms attached to the ring may be replaced. However, one, two or three optional substituents are preferred, whereas one or two optional substituents are even more preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention provides compounds of formula (I)

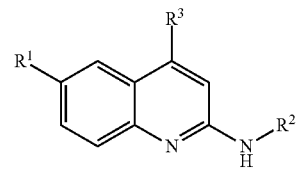

wherein
$R^1$ is —$NR^a$—$Ar^1$, —$NR^bCH_2$—$Ar^1$, —$CH_2NR^b$—$Ar^1$, —$NR^cC(O)$—$Ar^1$, —$OCH_2$—$Ar^1$, —$CH_2O$—$Ar^1$, —$CH_2CH_2$—$Ar^1$, —CH=CH—$Ar^1$, —NHC(O)NH—$Ar^1$, —$NHSO_2NH$—$Ar^1$, —$NR^cC(O)O$—$Ar^1$, —C(O)$NR^cCH_2$—$Ar^1$, —$CH_2NR^bCH_2$—$Ar^1$, —NHC(=N—$Ar^1$)—$Ar^1$, —$NR^bCH_2CH_2CH_2$—$Ar^1$, or —$NR^bCH_2CH_2O$—$Ar^1$,
$R^2$ is —$Ar^2$, —$CHR^d$—$Ar^2$, or —$CH_2CH_2O$—$Ar^2$,
$R^3$ is hydrogen,
phenyl or pyridinyl, optionally substituted with one or more $C_{1-4}$-alkyl, halo, or $C_{1-4}$-alkoxy,
—$NR^eR^f$, wherein $R^e$ and $R^f$ are each independently hydrogen or
—$(CH_2)_m$—$OR^g$, wherein m is from 2 to 6,
$Ar^1$ and $Ar^2$ are each independently aryl or heteroaryl, each optionally substituted by one or more B,
B is $C_{1-7}$-alkoxy,
$C_{1-7}$-haloalkoxy,
hydroxy,
halo,
$C_{1-7}$-alkyl, optionally substituted with one or more halo, hydroxy, or cyano,
—$S(O)_2$—$C_{1-7}$-alkyl,
—$NR^iR^{ii}$,
—$NR^{iii}S(O)_2R^{iv}$,
—$NR^{iii}C(O)R^{iv}$,
—$C(O)NR^{iii}R^{iv}$,
—$S(O)_2$—$NR^{iii}R^{iv}$, —CH$_2$—O—R$^v$,
—(OCH$_2$CH$_2$)$_n$—OR$^v$, wherein n is from 1 to 3,
—CH$_2$—(OCH$_2$CH$_2$)$_n$—OR$^v$, wherein n is from 1 to 3,
—C(O)R$^v$,
cyano,
nitro,
allyl,
C$_{3-7}$-cycloalkyl,
5- to 7-membered monocyclic heterocycloalkyl, or
two residues B in ortho-position to each other form a 3- to 4-membered bridge of the formula —CH$_2$CH$_2$CH$_2$—, —CH$_2$CH$_2$CH$_2$CH$_2$—, —O—C(R$^{vi}$)$_2$—O—, —OCH$_2$CH$_2$O—, —OCH(R$^{vii}$)CH(R$^{viii}$)—,
R$^a$, R$^b$, R$^c$, R$^d$, and R$^g$ are each independently hydrogen or C$_{1-7}$-alkyl;
R$^i$, R$^{ii}$, R$^{iii}$, R$^{iv}$, and R$^v$ are each independently hydrogen, C$_{1-7}$-alkyl or —(CH$_2$)$_n$—C$_{3-7}$-cycloalkyl, wherein n is from 0 to 3;
R$^{vi}$, R$^{vii}$, and R$^{viii}$ are each independently hydrogen, C$_{1-4}$-alkyl or halogen;
or a pharmaceutically acceptable salt thereof.

The 2-aminoquinolines of present invention can alternatively be described with formula I', indicating that the 2-amino-position as well as the 6-position of the quinoline core bear aromatic substituents Ar$^1$ and Ar$^2$, respectively, attached to the core with or without a linker X and Z:

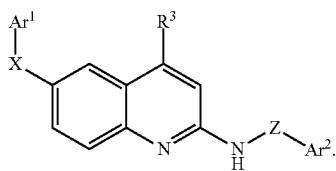

I'

The linker X is selected from —NR$^a$—, —NR$^b$CH$_2$—, —CH$_2$NR$^b$—, —NR$^c$C(O)—, —OCH$_2$—, —CH$_2$O—, —CH$_2$CH$_2$—, —CH═CH—, —NHC(O)NH—, —NHSO$_2$NH—, —NR$^c$C(O)O—, —C(O)NR$^c$CH$_2$—, —CH$_2$NR$^b$CH$_2$—, —NHC(═N—Ar$^1$)—, —NR$^b$CH$_2$CH$_2$CH$_2$—, and —NR$^b$CH$_2$CH$_2$O—. Ar$^1$R$^a$, R$^b$ and R$^c$ have the meaning as defined herein.

Further, the linker Z is a single bond, —CHR$^d$—, or —CH$_2$CH$_2$O—, with R$^d$ being hydrogen or C$_{1-7}$-alkyl, preferably hydrogen.

R$^3$ is as defined herein.

In the following, the compounds of present invention are described by way of formula I:

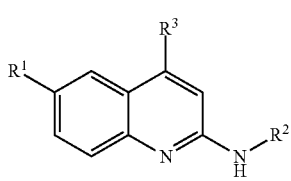

I

In certain embodiments of the invention, R$^1$ of the 2-aminoquinoline of the above-mentioned formula I is —NR$^a$—Ar$^1$, —NR$^b$CH$_2$—Ar$^1$, —CH$_2$NR$^b$—Ar$^1$, —NR$^c$C(O)—Ar$^1$, —OCH$_2$—Ar$^1$, —CH$_2$O—Ar$^1$, —CH$_2$CH$_2$—Ar$^1$, —CH═CH—Ar$^1$, —NHC(O)NH—Ar$^1$, —NHSO$_2$NH—Ar$^1$, —NR$^c$C(O)O—Ar$^1$, —C(O)NR$^c$CH$_2$—Ar$^1$, —CH$_2$NR$^b$CH$_2$—Ar$^1$, —NHC(═N—Ar$^1$)—Ar$^1$, —NR$^b$CH$_2$CH$_2$CH$_2$—Ar$^1$, or —NR$^b$CH$_2$CH$_2$O—Ar$^1$.

In preferred embodiments of the invention, R$^1$ of the 2-aminoquinoline of formula I is —NR$^a$—Ar$^1$, —NR$^b$CH$_2$—Ar$^1$, —CH$_2$NR$^b$—Ar$^1$, —OCH$_2$—Ar$^1$, —CH$_2$O—Ar$^1$, —CH$_2$CH$_2$—Ar$^1$, —CH═CH—Ar$^1$, —NHC(O)NH—Ar$^1$, —NHSO$_2$NH—Ar$^1$, —NR$^c$C(O)O—Ar$^1$, —NR$^b$CH$_2$CH$_2$CH$_2$—Ar$^1$, or —NR$^b$CH$_2$CH$_2$O—Ar$^1$.

Also preferred embodiments of the invention encompass the compound of formula I with R$^1$ being —NR$^a$—Ar$^1$, —NR$^b$CH$_2$—Ar$^1$, —CH$_2$O—Ar$^1$, —CH$_2$CH$_2$—Ar$^1$, —CH═CH—Ar$^1$, —NHC(O)NH—Ar$^1$, —NHSO$_2$NH—Ar$^1$, or —NR$^c$C(O)O—Ar$^1$.

Also preferred embodiments of the invention encompass the compound of formula I with R$^1$ being —NR$^a$—Ar$^1$, —NR$^b$CH$_2$—Ar$^1$, —CH$_2$O—Ar$^1$, —CH$_2$CH$_2$—Ar$^1$, —CH═CH—Ar$^1$, —NHSO$_2$NH—Ar$^1$, or —NR$^c$C(O)O—Ar$^1$.

In all these embodiments, R$^a$, R$^b$ and R$^c$ are each independently hydrogen or C$_{1-7}$-alkyl; preferably, R$^a$, R$^b$, and R$^c$ are hydrogen.

In certain embodiments of the invention, R$^1$ of the compound of formula I is —NH—Ar$^1$.
In certain embodiments of the invention, R$^1$ of the compound of formula I is —NHCH$_2$—Ar$^1$.
In certain embodiments of the invention, R$^1$ of the compound of formula I is —CH$_2$O—Ar$^1$.
In certain embodiments of the invention, R$^1$ of the compound of formula I is —CH$_2$CH$_2$—Ar$^1$.
In certain embodiments of the invention, R$^1$ of the compound of formula I is —CH═CH—Ar$^1$.
In certain embodiments of the invention, R$^1$ of the compound of formula I is NHC(O)NH—Ar$^1$.
In certain embodiments of the invention, R$^1$ of the compound of formula I is —NHSO$_2$NH—Ar$^1$.
In certain embodiments of the invention, R$^1$ of the compound of formula I is —NHC(O)O—Ar$^1$.

It is to be understood that all combinations of these embodiments are encompassed with present invention.

In certain embodiments of the invention, Ar$^1$ is an aryl or heteroaryl moiety as defined herein, each optionally substituted by one or more B, also as defined herein.

Preferably, Ar$^1$ is phenyl, naphthyl, an aromatic 5- or 6-membered monocyclic heteroaryl or an aromatic 9- or 10-membered bicyclic heteroaryl, each containing one, two, three or four heteroatoms selected from N, O or S, the remaining ring atoms being C. Again, Ar$^1$ is optionally substituted by one or more B as defined herein.

Examples for Ar$^1$ are phenyl, naphthyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, tetrazolyl, indolyl, benzofuranyl, benzothiophenyl, benzimidazolyl, benzoxyzolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phtalazinyl, or pteridinyl, each optionally substituted with one or more B as defined herein.

Preferred examples for Ar$^1$ are phenyl, tetrazolyl, [1,3,4]-oxadiazolyl, [1,2,4]-oxadiazolyl, imidazolyl, oxazolyl, isoxazolyl, furanyl, pyridinyl, pyrimidinyl or benzoxazolyl, each optionally substituted with one of more B as defined herein above.

Preferred optional substituents B are:
C$_{1-7}$-alkoxy,
C$_{1-7}$-haloalkoxy,
halo, $C_{1-7}$-alkyl, optionally substituted with one or more halo, or hydroxy,
—$CH_2$—O—$R^v$,
—$(OCH_2CH_2)_n$—$OR^v$, wherein n is from 1 to 3,
—$CH_2$—$(OCH_2CH_2)_n$—$OR^v$, wherein n is from 1 to 3,
$C_{3-7}$-cycloalkyl,
5- to 7-membered monocyclic heterocycloalkyl, preferably piperidinyl, or
two residues B in ortho-position to each other forming a —O—$C(R^{vi})_2$—O— bridge;
wherein $R^v$ is as defined above, preferably $R^v$ is methyl;
and wherein $R^{vi}$ is as defined above, preferably $R^{vi}$ is hydrogen.

Even more preferred optional substituents B are:
$C_{1-7}$-alkoxy,
$C_{1-7}$-haloalkoxy,
halo,
$C_{1-7}$-alkyl, optionally substituted with one or more halo, or hydroxy,
—$CH_2$—O—$R^v$,
—$(OCH_2CH_2)_n$—$OR^v$, wherein n is from 1 to 3,
—$CH_2$—$(OCH_2CH_2)_n$—$OR^v$, wherein n is from 1 to 3,
$C_{3-7}$-cycloalkyl, or
piperidinyl;
wherein $R^v$ is as defined above, preferably $R^v$ is methyl.

In certain embodiments of the invention, $R^2$ of the 2-aminoquinoline of the above-mentioned formula I is —$Ar^2$, —$CHR^d$—$Ar^2$, or —$CH_2CH_2O$—$Ar^2$. Thereby, $R^d$ is selected from hydrogen or $C_{1-7}$-alkyl. Preferably, $R^d$ is hydrogen.

In a preferred embodiment of the invention, $R^2$ of the 2-aminoquinoline of the above-mentioned formula I is —$CH_2$—$Ar^2$ or —$CH_2CH_2O$—$Ar^2$.

In certain embodiments of the invention, $Ar^2$ is an aryl or heteroaryl moiety as defined herein, each optionally substituted by one or more B, also as defined herein.

Preferably, $Ar^2$ is phenyl, naphthyl, an aromatic 5- or 6-membered monocyclic heteroaryl or an aromatic 9- or 10-membered bicyclic heteroaryl, each containing one, two, three or four heteroatoms selected from N, O or S, the remaining ring atoms being C. Again, $Ar^2$ is optionally substituted by one or more B as defined herein.

Examples for $Ar^2$ are phenyl, naphthyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, tetrazolyl, indolyl, benzofuranyl, benzothiophenyl, benzimidazolyl, benzoxyzolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phtalazinyl, or pteridinyl, each optionally substituted with one or more B as defined herein.

Preferred examples for $Ar^2$ are phenyl, tetrazolyl, [1,3,4]-oxadiazolyl, [1,2,4]-oxadiazolyl, imidazolyl, oxazolyl, isoxazolyl, furanyl, pyridinyl, pyrimidinyl or benzoxazolyl, each optionally substituted with one of more B as defined herein, for instance as defined in claim 1.

Even more preferred examples for $Ar^2$ are phenyl, pyridinyl, or furanyl, each optionally substituted with one or more B as defined herein.

Preferred optional substituents B are:
$C_{1-7}$-alkoxy,
$C_{1-7}$-haloalkoxy,
halo, $C_{1-7}$-alkyl, optionally substituted with one or more halo, or hydroxy,
—$CH_2$—O—$R^v$,
—$(OCH_2CH_2)_n$—$OR^v$, wherein n is from 1 to 3, —$CH_2$—$(OCH_2CH_2)_n$—$OR^v$, wherein n is from 1 to 3, $C_{3-7}$-cycloalkyl,
5- to 7-membered monocyclic heterocycloalkyl, preferably piperidinyl, or
two residues B in ortho-position to each other forming a —O—$C(R^{vi})_2$—O— bridge;
wherein $R^v$ is as defined above, preferably $R^v$ is methyl;
and wherein $R^{vi}$ is as defined above, preferably $R^{vi}$ is hydrogen.

Even more preferred optional substituents B are:
$C_{1-7}$-alkoxy,
halo,
$C_{1-7}$-alkyl, optionally substituted with one or more halo, or
two residues B in ortho-position to each other forming a —O—$C(R^{vi})_2$—O— bridge,
wherein $R^{vi}$ is as defined above, and preferably is hydrogen.

In certain embodiments of the invention, $R^3$ of the 2-aminoquinoline of the above-mentioned formula I is
hydrogen,
phenyl or pyridinyl, optionally substituted with one or more $C_{1-4}$-alkyl, halo, or $C_{1-4}$-alkoxy,
—$NR^eR^f$, wherein $R^e$ and $R^f$ are each independently hydrogen, or —$(CH_2)_m$—$OR^g$,
wherein m is from 2 to 6, and $R^g$ is hydrogen or $C_{1-7}$-alkyl, preferably $R^g$ is hydrogen.

In preferred embodiments of the invention, $R^3$ of formula I is
hydrogen, or
phenyl or pyridinyl, optionally substituted with one or more $C_{1-4}$-alkyl, halo, or $C_{1-4}$-alkoxy.

In a preferred embodiment of the invention, $R^3$ of formula I is hydrogen.

It is understood that all of the embodiments described above may be combined with each other.

As an example for such a combination, one of the preferred embodiments of the invention is concerned with compounds of formula I

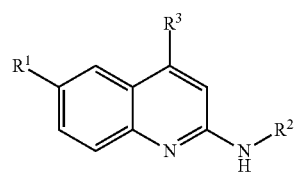

wherein
$R^1$ is —$NR^a$—$Ar^1$, —$NR^bCH_2$—$Ar^1$, —$CH_2O$—$Ar^1$, —$CH_2CH_2$—$Ar^1$, —$CH$=$CH$—$Ar^1$, —$NHC(O)NH$—$Ar^1$, —$NHSO_2NH$—$Ar^1$, or —$NR^cC(O)O$—$Ar^1$.
$R^2$ is —$Ar^2$, —$CH_2$—$Ar^2$, or —$CH_2CH_2O$—$Ar^2$,
$R^3$ is hydrogen, or
phenyl or pyridinyl, optionally substituted with one or more $C_{1-4}$-alkyl, halo, or $C_{1-4}$-alkoxy,
$Ar^1$ and $Ar^2$ are each independently phenyl, naphthyl, aromatic 5- or 6-membered monocyclic heteroaryl or aromatic 9- or 10-membered bicyclic heteroaryl, wherein each heteroaryl contains one, two, three or four heteroatoms selected from N, O and S, the remaining ring atoms being C, each $Ar^1$ and $Ar^2$ is optionally and independently substituted by one or more B, B is $C_{1-7}$-alkoxy,
$C_{1-7}$-haloalkoxy,
hydroxy,
halo,
$C_{1-7}$-alkyl, optionally substituted with one or more halo, hydroxy, or cyano,
—$S(O)_2$—$C_{1-7}$-alkyl,
—$NR^iR^{ii}$,
—$NR^{iii}S(O)_2R^{iv}$,
—$NR^{iii}C(O)R^{iv}$,
—$C(O)NR^{iii}R^{iv}$,
—$S(O)_2$—$NR^{iii}R^{iv}$,
—$CH_2$—O—$R^v$,
—$(OCH_2CH_2)_n$—$OR^v$, wherein n is from 1 to 3,
—$CH_2$—$(OCH_2CH_2)_n$—$OR^v$, wherein n is from 1 to 3,
—$C(O)R^v$,
cyano,
nitro,
allyl,
$C_{3-7}$-cycloalkyl,
5- to 7-membered monocyclic heterocycloalkyl, or
two residues B in ortho-position to each other form a 3- to 4-membered bridge of the formula —$CH_2CH_2CH_2$—, —$CH_2CH_2CH_2CH_2$—, —$OCH_2CH_2O$—, —$OCH(R^{vii})CH(R^{viii})$—, $R^a$, $R^b$, $R^c$, and $R^g$ are each independently hydrogen or $C_{1-7}$-alkyl;

$R^i$, $R^{ii}$, $R^{iii}$, $R^{iv}$, and $R^v$ are each independently hydrogen, $C_{1-7}$-alkyl or —$(CH_2)_n$—$C_{3-7}$-cycloalkyl, wherein n is from 0 to 3;

$R^{vi}$, $R^{vii}$, and $R^{viii}$ are each independently hydrogen, $C_{1-4}$-alkyl or halogen;

or a pharmaceutically acceptable salt thereof.

Preferred compounds of present invention are those as exemplified in the examples.

Even more preferred are compounds selected from
N2-(2-phenoxy-ethyl)-N6-pyridin-3-ylmethyl-quinoline-2,6-diamine,
(2-methoxy-benzyl)-(6-phenethyl-quinolin-2-yl)-amine,
N2-(2-methoxy-benzyl)-N6-pyridin-3-ylmethyl-quinoline-2,6-diamine,
N2-(2-phenoxy-ethyl)-N6-pyridin-4-ylmethyl-quinoline-2,6-diamine,
N6-benzyl-N2-(2-methoxy-benzyl)-quinoline-2,6-diamine,
N6-(2-methoxy-benzyl)-N2-(2-phenoxy-ethyl)-quinoline-2,6-diamine,
N6-(3-methoxy-benzyl)-N2-(2-phenoxy-ethyl)-quinoline-2,6-diamine,
N2-(2-methoxy-benzyl)-4-phenyl-N6-pyridin-3-ylmethyl-quinoline-2,6-diamine,
(2-methoxy-benzyl)-[6-((E)-2-pyridin-3-yl-vinyl)-quinolin-2-yl]-amine,
N2,N6-bis-(2-methoxy-benzyl)-quinoline-2,6-diamine,
N6-(3-methoxy-benzyl)-N2-(2-methoxy-benzyl)-quinoline-2,6-diamine,
N2-(2-methoxy-benzyl)-N6-(2-trifluoromethoxy-benzyl)-quinoline-2,6-diamine,
(2-methoxy-benzyl)-[6-(2-pyridin-3-yl-ethyl)-quinolin-2-yl]-amine,
N6-(3-methoxy-benzyl)-N2-(2-methoxy-benzyl)-4-phenyl-quinoline-2,6-diamine,
N2,N6-bis-(2-methoxy-benzyl)-4-phenyl-quinoline-2,6-diamine,
N2-(2-methoxy-benzyl)-N6-(5-methyl-furan-2-ylmethyl)-quinoline-2,6-diamine,
N2-(2-methoxy-benzyl)-N6-(3-methyl-3H-imidazol-4-ylmethyl)-quinoline-2,6-diamine,
N2-(5-methyl-furan-2-ylmethyl)-N6-pyridin-3-ylmethyl-quinoline-2,6-diamine,
N6-(2-methoxy-benzyl)-N2-(5-methyl-furan-2-ylmethyl)-quinoline-2,6-diamine,
N6-(3-methoxy-benzyl)-N2-(5-methyl-furan-2-ylmethyl)-quinoline-2,6-diamine,
N6-benzyl-N2-(5-methyl-furan-2-ylmethyl)-quinoline-2,6-diamine,
N2-(4-fluoro-2-methoxy-benzyl)-4-phenyl-N6-pyridin-3-ylmethyl-quinoline-2,6-diamine,
N2-(2-methoxy-benzyl)-N6-pyridin-3-ylmethyl-4-o-tolyl-quinoline-2,6-diamine,
N-2-(2-methoxy-benzyl)-4-(3-methoxy-phenyl)-N-6-pyridin-3-ylmethyl-quinoline-2,6-diamine,
4-(2,5-difluoro-phenyl)-N2-(2-methoxy-benzyl)-N6-pyridin-3-ylmethyl-quinoline-2,6-diamine,
N-6-benzyl-N-2-(4-fluoro-2-methoxy-benzyl)-4-phenyl-quinoline-2,6-diamine,
N-2-(4-fluoro-2-methoxy-benzyl)-4-phenyl-N-6-&-pyridin-4-ylmethyl-quinoline-2,6-diamine,
N-6-2-benzyl-N-2-(4-fluoro-2-methoxy-benzyl)-4-o-tolyl-quinoline-2,6-diamine,
N-2-(4-fluoro-2-methoxy-benzyl)-N-6-pyridin-4-ylmethyl-4-o-tolyl-quinoline-2,6-diamine,
(2-methoxy-benzyl)-(6-phenoxymethyl-quinolin-2-yl)-amine,
N6-benzyl-N2-(4-fluoro-2-methoxy-benzyl)-quinoline-2,4,6-triamine,
N2-(4-fluoro-2-methoxy-benzyl)-N6-(2-methoxy-benzyl)-quinoline-2,4,6-triamine,
N6-benzyl-N2-(2-methoxy-benzyl)-quinoline-2,4,6-triamine,
N2,N6-bis-(2-methoxy-benzyl)-quinoline-2,4,6-triamine,
N2-(2-methoxy-benzyl)-N6-pyridin-3-ylmethyl-quinoline-2,4,6-triamine,
N2-(5-methyl-furan-2-ylmethyl)-N6-pyridin-3-ylmethyl-quinoline-2,4,6-triamine,
N6-benzyl-N2-(5-methyl-furan-2-ylmethyl)-quinoline-2,4,6-triamine,
N6-benzyl-N2-(3-methoxy-benzyl)-quinoline-2,6-diamine,
N2-(3-methoxy-benzyl)-N6-pyridin-3-ylmethyl-quinoline-2,6-diamine,
N6-benzyl-N2-(5-fluoro-2-methoxy-benzyl)-quinoline-2,4,6-triamine,
N2-(5-fluoro-2-methoxy-benzyl)-N6-pyridin-3-ylmethyl-quinoline-2,4,6-triamine,
N2-(5-fluoro-2-methoxy-benzyl)-N6-pyridin-3-ylmethyl-quinoline-2,6-diamine,
N2-(5-methyl-furan-2-ylmethyl)-N6-(3-trifluoromethyl-phenyl)-quinoline-2,6-diamine,
N2-benzo[1,3]dioxol-4-ylmethyl-N6-pyridin-3-ylmethyl-quinoline-2,6-diamine,
1-[2-(2-methoxy-benzylamino)-quinolin-6-yl]-3-(4-methoxy-phenyl)-urea,
[2-(2-methoxy-benzylamino)-quinolin-6-yl]-carbamic acid 4-methoxy-phenyl ester,
N-(4-fluorophenyl)-N'-{2-[(2-methoxybenzyl)amino]quinolin-6-yl}sulfamide,
N2-(2-methoxy-benzyl)-N6-pyrimidin-2-yl-quinoline-2,6-diamine,
N2-(2-methoxy-benzyl)-N6-(5-methyl-[1,3,4]oxadiazol-2-yl)-quinoline-2,6-diamine, N2-(2-methoxy-benzyl)-N6-(3-methyl-[1,2,4]oxadiazol-5-yl)-quinoline-2,6-diamine, N6-(2-ethyl-2H-tetrazol-5-yl)-N2-(2-methoxy-benzyl)-quinoline-2,6-diamine, N2-(2-methoxy-benzyl)-N6-(5-methyl-isoxazol-3-yl)-quinoline-2,6-diamine, N6-(4,6-dimethyl-pyrimidin-2-yl)-N2-(2-methoxy-benzyl)-quinoline-2,6-diamine, N2-(2-methoxy-benzyl)-N6-(4-methyl-pyrimidin-2-yl)-quinoline-2,6-diamine, N2-(2-methoxy-benzyl)-N6-pyridin-2-yl-quinoline-2,6-diamine, N2-(2-methoxy-benzyl)-N6-(6-methyl-pyridin-2-yl)-quinoline-2,6-diamine, N2-(2-methoxy-benzyl)-N6-(4-trifluoromethyl-pyrimidin-2-yl)-quinoline-2,6-diamine, N6-(2-tert-butyl-2H-tetrazol-5-yl)-N2-(2-methoxy-benzyl)-quinoline-2,6-diamine, N6-(5-cyclopropyl-[1,3,4]oxadiazol-2-yl)-N2-(2-methoxy-benzyl)-quinoline-2,6-diamine, N2-(2-methoxy-benzyl)-N6-(5-trifluoromethyl-[1,3,4]oxadiazol-2-yl)-quinoline-2,6-diamine, N2-(2-methoxy-benzyl)-N6-(5-trifluoromethyl-oxazol-2-yl)-quinoline-2,6-diamine, N2-(2-methoxy-benzyl)-N6-oxazol-2-yl-quinoline-2,6-diamine, N2-(2-methoxy-benzyl)-N6-(6-trifluoromethyl-pyridin-2-yl)-quinoline-2,6-diamine, 2-{3-[2-(2-methoxy-benzylamino)-quinolin-6-ylamino]-phenyl}-ethanol, and N2-(2,2-dimethyl-2,3-dihydro-benzofuran-7-yl)-$N^6$-(6-methyl-pyridin-2-yl)-quinoline-2,6-diamine.

The present compounds of formula I, their starting materials, their pharmaceutically acceptable salts, and their optical isomers can be prepared by methods known in the art. These methods are described below in routes 1 to 17. As an example, a process may be used to prepare some of the preferred compounds, which comprises one of the following steps:

A process to prepare the compound of formula I,

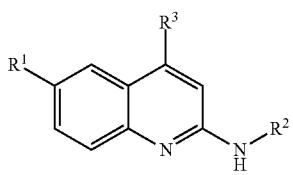

wherein $R^1$ is —NH—$Ar^1$, —NHCH$_2$—$Ar^1$, —NHCH$_2$CH$_2$CH$_2$—$Ar^1$, or —NHCH$_2$CH$_2$O—$Ar^1$, $R^2$ is —$Ar^2$, —CH$_2$—$Ar^2$, or —CH$_2$CH$_2$O—$Ar^2$, $R^3$ is hydrogen or phenyl or pyridinyl, optionally substituted with one or more $C_{1-4}$-alkyl, halo, or $C_{1-4}$-alkoxy, and $Ar^1$ and $Ar^2$ are as defined above, comprising the steps of (a) reacting a compound of formula 1

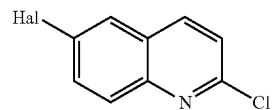

wherein Hal is Cl or Br, with an amine $R^2$—NH$_2$ to give a compound of formula 2

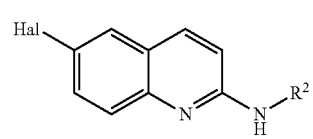

(b) followed by palladium catalyzed substitution reaction with the amines $Ar^1NH_2$, $Ar^1$—CH$_2$—NH$_2$, $Ar^1$—CH$_2$CH$_2$CH$_2$—NH$_2$, or $Ar^1$—OCH$_2$CH$_2$—NH$_2$;

and, if desired, converting the compounds obtained into pharmaceutically acceptable acid addition salts.

Biological Tests:

As mentioned earlier, the compounds of formula I or formula I' and their pharmaceutically acceptable addition salts possess valuable pharmaceutical properties. The compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H] LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells.

Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Nonspecific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calculated using the Cheng-Prussoff equation.

The affinity towards the human 5-HT$_{5A}$ receptor of the compounds according to the invention is exemplified in the table below:

| Ex. # | Ki/µM | Ex. # | Ki/µM | Ex. # | Ki/µM | Ex. # | Ki/µM |
|---|---|---|---|---|---|---|---|
| 1 | 0.022 | 18 | 0.087 | 36 | 0.042 | 73 | 0.027 |
| 4 | 0.104 | 19 | 0.022 | 37 | 0.040 | 79 | 0.030 |
| 6 | 0.027 | 20 | 0.030 | 38 | 0.041 | 80 | 0.087 |
| 7 | 0.101 | 23 | 0.129 | 42 | 0.169 | 81 | 0.040 |
| 8 | 0.022 | 25 | 0.022 | 43 | 0.073 | 87 | 0.044 |
| 9 | 0.026 | 27 | 0.030 | 44 | 0.040 | 88 | 0.026 |
| 10 | 0.042 | 28 | 0.044 | 47 | 0.030 | 90 | 0.033 |
| 13 | 0.011 | 29 | 0.032 | 49 | 0.128 | 92 | 0.034 |
| 14 | 0.060 | 31 | 0.017 | 51 | 0.015 | 94 | 0.030 |
| 15 | 0.017 | 32 | 0.012 | 54 | 0.022 | 96 | 0.047 |
| 16 | 0.017 | 33 | 0.050 | 55 | 0.022 | 101 | 0.035 |
| 17 | 0.025 | 35 | 0.022 | 57 | 0.037 | 103 | 0.025 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation

Wet Granulation

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I may be prepared as shown in the following description:

Chemical Synthesis of the Compounds

In examples 1-104 and in the following schemes 1 to 17 the preparation of the compounds of formula I or formula I' are described in more detail. The starting materials are known compounds or can be prepared according to methods known in the art.

Compounds of formula I can be prepared in accordance with the following routes:

Scheme 1: Route 1 described in example 1

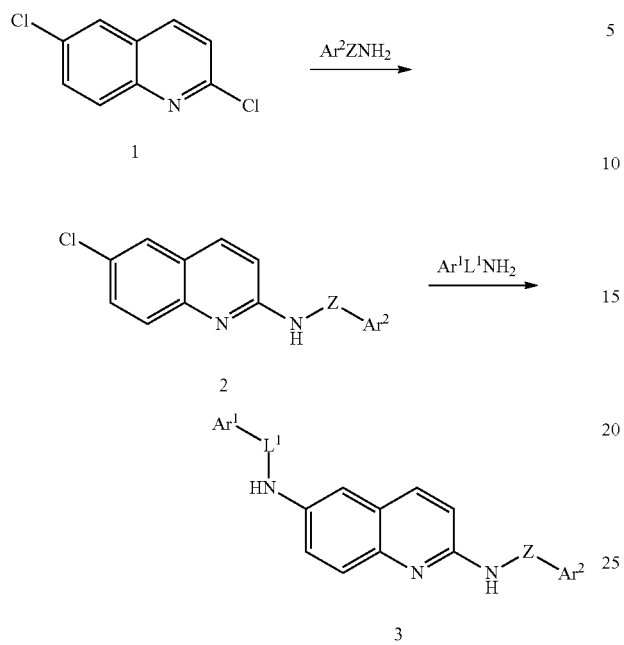

2,6-Dichloroquinoline (1) is reacted with 2 equivalents of an amine $Ar^2ZNH_2$ without solvent. Intermediate 2 is reacted with an amine $Ar^1L^1NH_2$ in a palladium catalyzed substitution reaction. $Ar^1L^1NH_2$ in this context means $Ar^1$—$CH_2$—$NH_2$, $Ar^1$—$CH_2CH_2CH_2$—$NH_2$, or $Ar^1$—$OCH_2CH_2$—$NH_2$.

Scheme 2: Route 2 described in example 2

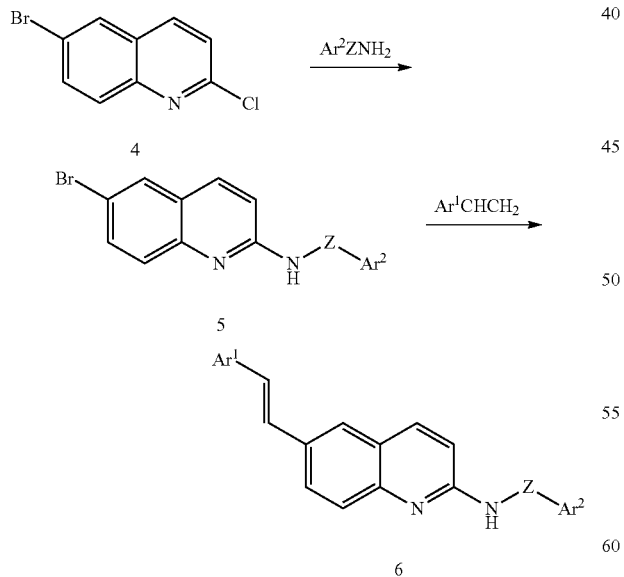

6-Bromo-2-chloroquinoline (4) is reacted with 2 equivalents of an amine $Ar^2ZNH_2$ without solvent. Intermediate 5 is reacted with an alkene $Ar^1CH=CH_2$ in a palladium catalyzed substitution reaction.

Scheme 3: Route 3 described in example 3

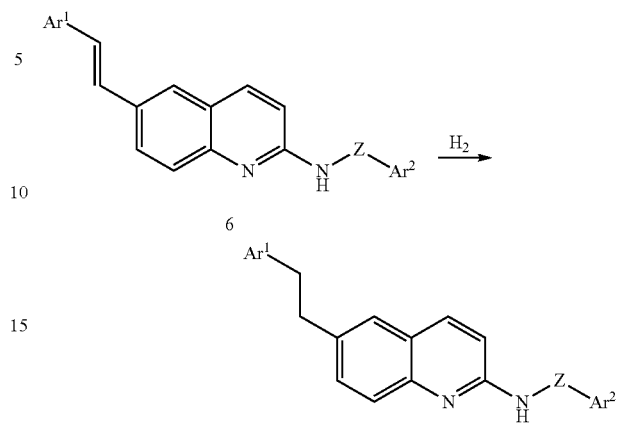

Compounds of the general structure 6 are reacted with hydrogen in presence of a palladium catalyst.

Scheme 4: Route described in example 13

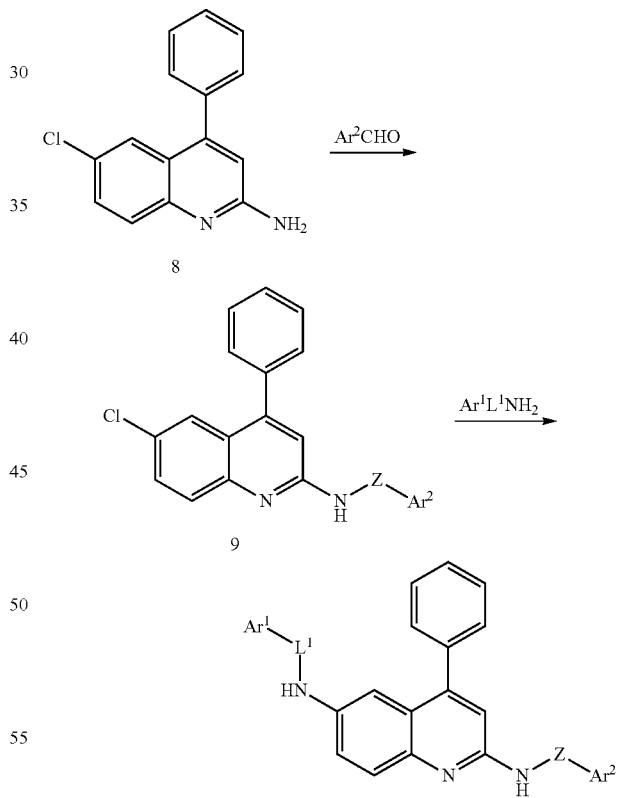

6-Chloro-4-phenyl-quinolin-2-ylamine (8) is reacted with 2 equivalents of an amine $Ar^2ZNH_2$ without solvent. Intermediate 8 is reacted with an aldehyde $Ar^2CHO$ in a reductive amination. Intermediate 9 is reacted with an amine $Ar^1L^1NH_2$ in a palladium catalyzed substitution reaction. $Ar^1L^1NH_2$ in this context means $Ar^1$—$CH_2$—$NH_2$, $Ar^1$—$CH_2CH_2CH_2$—$NH_2$, or $Ar^1$—$OCH_2CH_2$—$NH_2$.

Scheme 5: Route 5 described in example 14

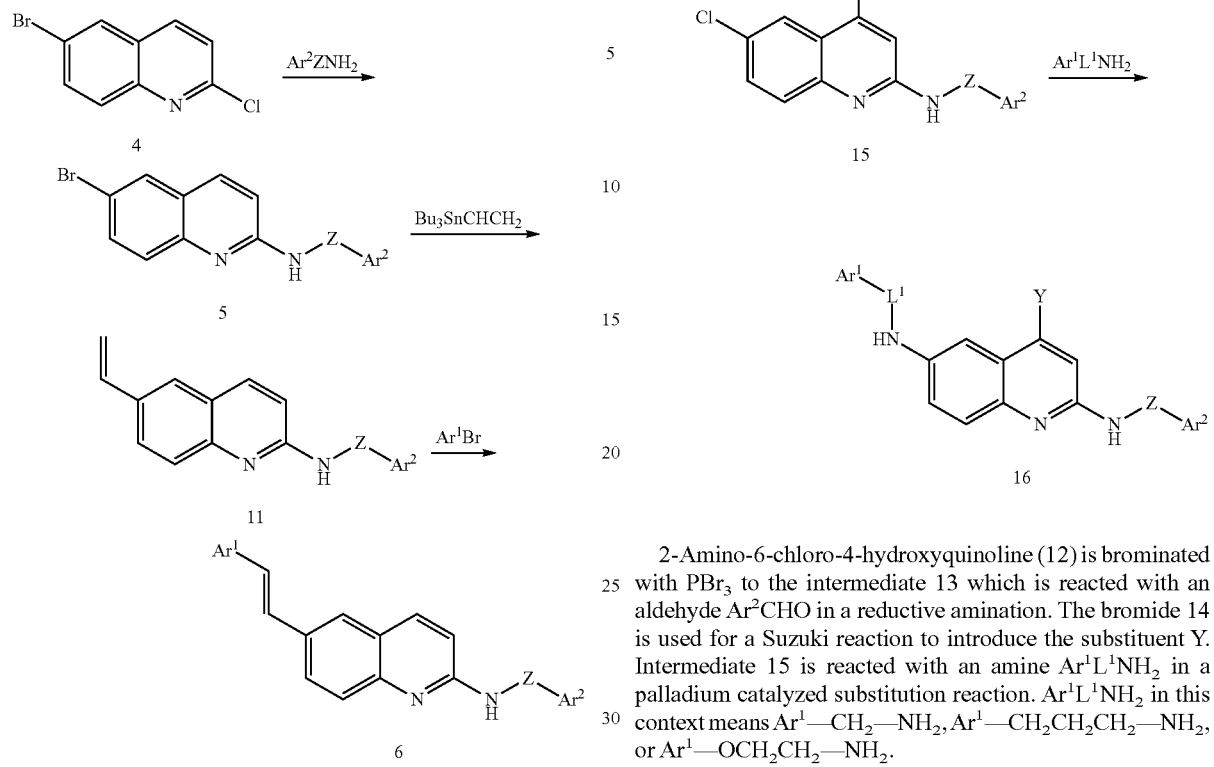

6-Bromo-2-chloroquinoline (4) is reacted with 2 equivalents of an amine Ar²ZNH₂ without solvent. Intermediate 5 is reacted with vinyltributyltin in a palladium catalyzed substitution reaction. Intermediate 11 is reacted with an arylbromide or aryliodide Ar¹hal in a palladium catalyzed substitution reaction.

Scheme 6: Route 6 described in example 30

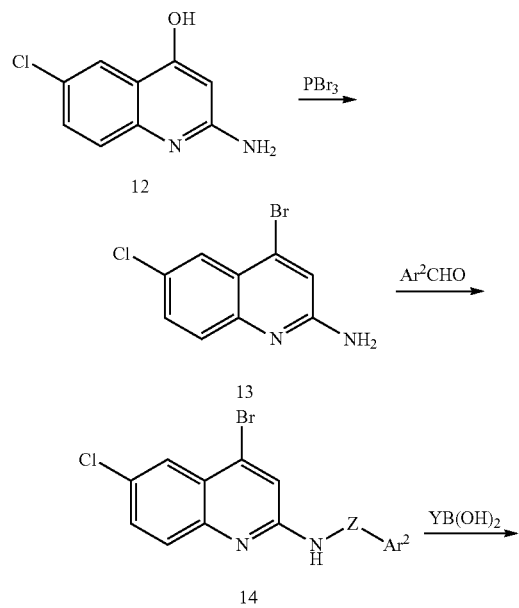

2-Amino-6-chloro-4-hydroxyquinoline (12) is brominated with PBr₃ to the intermediate 13 which is reacted with an aldehyde Ar²CHO in a reductive amination. The bromide 14 is used for a Suzuki reaction to introduce the substituent Y. Intermediate 15 is reacted with an amine Ar¹L¹NH₂ in a palladium catalyzed substitution reaction. Ar¹L¹NH₂ in this context means Ar¹—CH₂—NH₂, Ar¹—CH₂CH₂CH₂—NH₂, or Ar¹—OCH₂CH₂—NH₂.

Scheme 7: Route 7 described in example 40

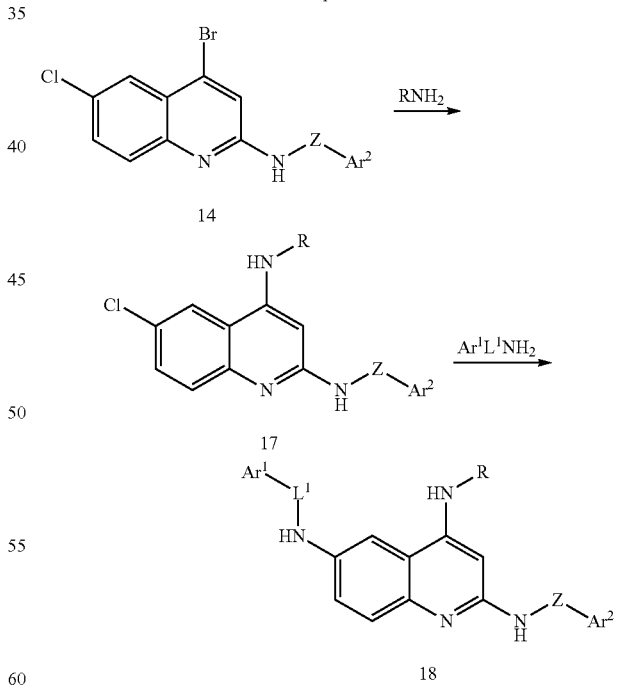

Intermediate (14) is sequentially reacted with an amine RNH₂ and an amine Ar¹L¹NH₂ in a palladium catalyzed substitution reaction using two different catalyst systems. Ar¹L¹NH₂ in this context means Ar¹—CH₂—NH₂, Ar¹—CH₂CH₂CH₂—NH₂, or Ar¹—OCH₂CH₂—NH₂.

Scheme 8: Route 8 described in example 43

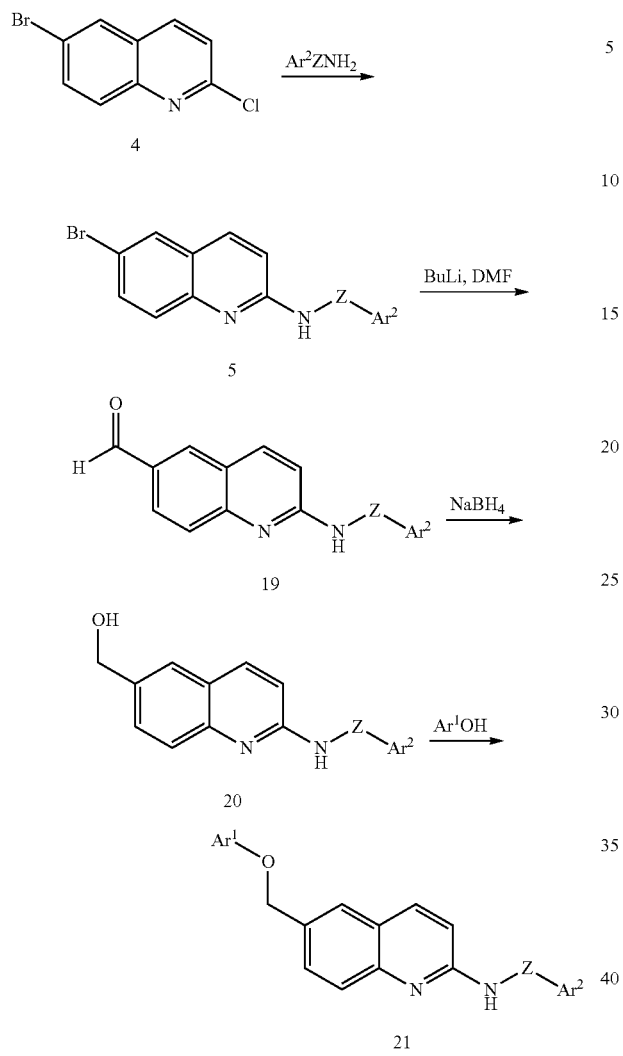

6-Bromo-2-chloroquinoline (4) is reacted with 2 equivalents of an amine $Ar^2ZNH_2$ without solvent. Intermediate 5 is reacted with n-butyllithium and quenched with dimethylformamide to produce aldehyde 19 which is reduced with sodium borohydride to the alcohol 20. Alcohol 20 is then reacted in a Mitsunobu reaction with a phenol derivative $Ar^1OH$.

Scheme 9: Route 9 described in example 44

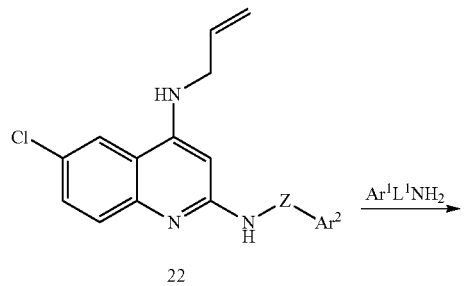

-continued

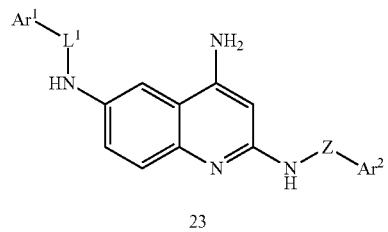

Intermediate (22) is reacted with an amine $Ar^1L^1NH_2$ in a palladium catalyzed substitution reaction. The allyl protecting group is lost during this reaction. $Ar^1L^1NH_2$ in this context means $Ar^1$—$CH_2$—$NH_2$, $Ar^1$—$CH_2CH_2CH_2$—$NH_2$, or $Ar^1$—$OCH_2CH_2$—$NH_2$.

Scheme 10: Route 10 described in example 49

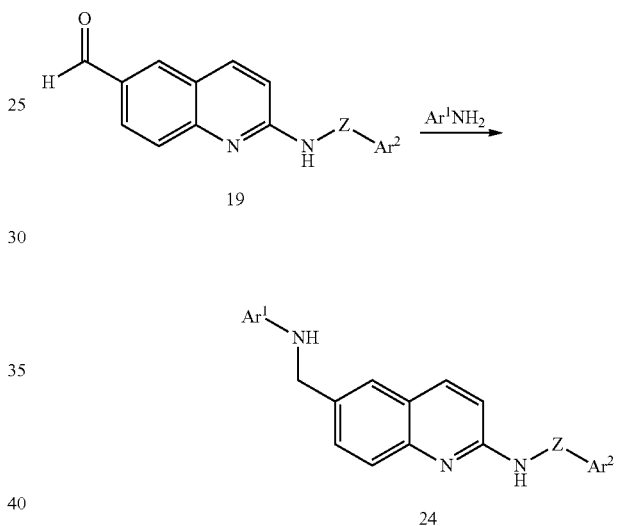

Aldehyde 19 is reacted with an amine $ArNH_2$ in a reductive amination.

Scheme 11: Route 11 described in example 61

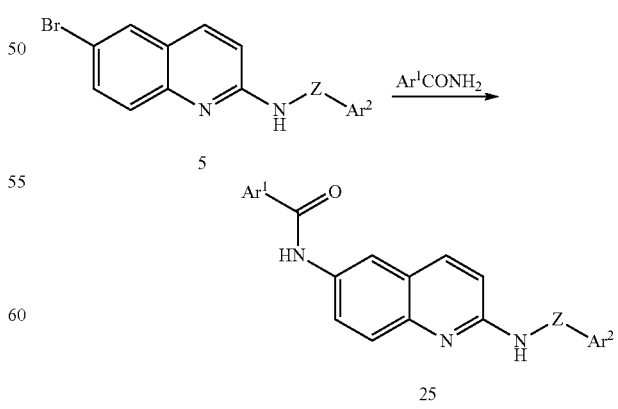

Intermediate 5 is reacted with an amide $Ar^1CONH_2$ in a palladium catalyzed substitution reaction.

Scheme 12: Route 12 described in example 69

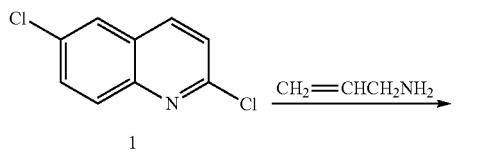

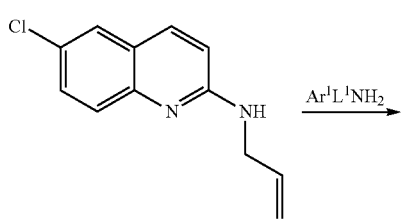

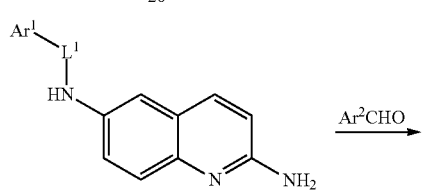

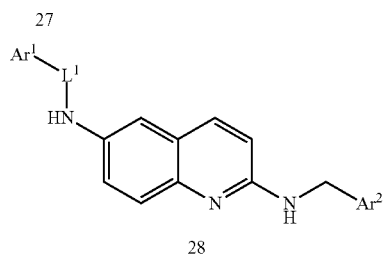

2,6-Dichloroquinoline (1) is reacted with 2 equivalents of allylamine without solvent. Intermediate 26 is reacted with an amine Ar¹L¹NH₂ in a palladium catalyzed substitution reaction. Ar¹L¹NH₂ in this context means Ar¹—CH₂—NH₂, Ar¹—CH₂CH₂CH₂—NH₂, or Ar¹—OCH₂CH₂—NH₂. The allyl protecting group is lost in this transformation. Intermediate 27 is reacted with an aldehyde Ar²CHO in a reductive amination Scheme 13: Route 13 described in example 74

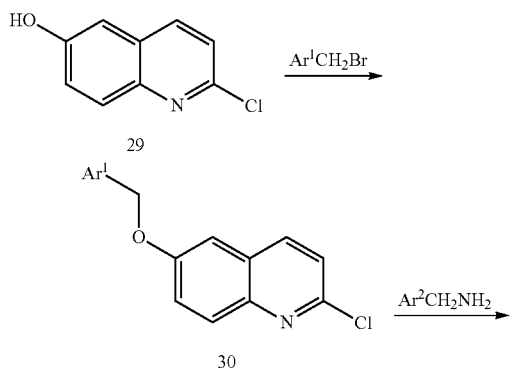

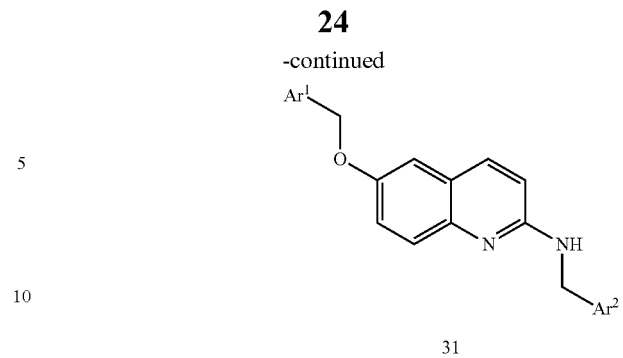

2-Chloro-6-hydroxy-quinolin (29, CAS-RN 577967-89-6) is reacted with benzyl bromides in acetone under potassium carbonate conditions to yield 6-benzyloxy derivative (30). In a subsequent step benzyl amines are introduced in position 2.

Scheme 14: Route 14 described in example 82

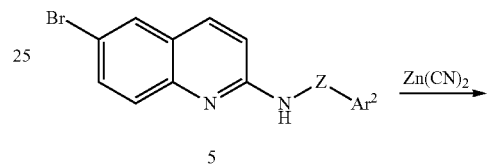

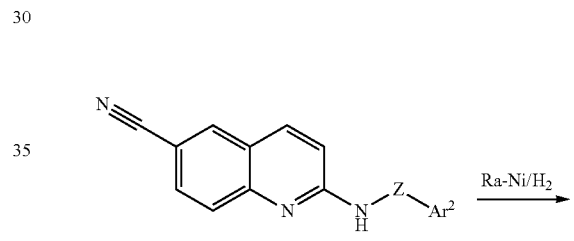

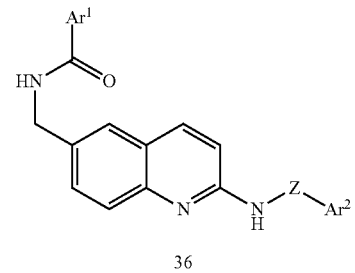

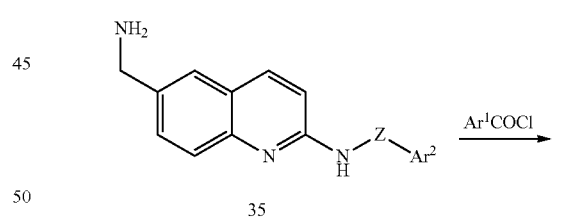

Intermediates 5 (see route 2) are reacted with zinc cyanide in a palladium catalyzed substitution reaction. The cyano group in 34 is reduced with hydrogen to the amines 35.

Amines 35 are reacted with a benzoyl chloride (Ar¹COCl).

Scheme 15: Route 15 described in example 83

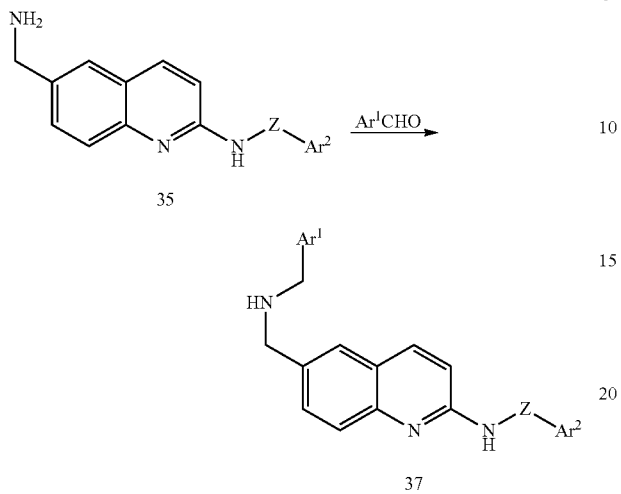

Reductive amination of benzaldehydes Ar¹CHO with amines 35.

Scheme 16: Route 16 described in example 84

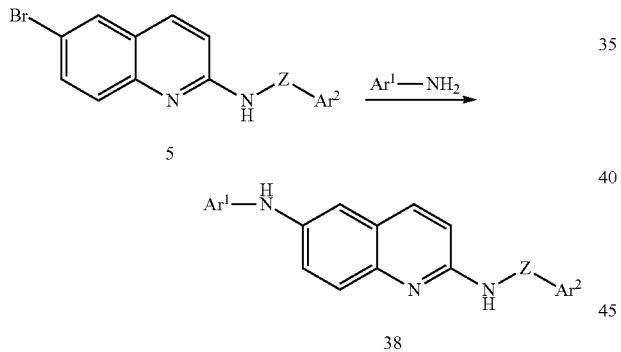

Intermediates 5 (see route 2) are reacted with hetero-aromatic amines in a palladium catalyzed substitution reaction.

Scheme 17: Route 17 described in example 77-81

2-Chloro-6-nitro-quinoline (cas no.: 29969-57-1) is treated with ortho methoxybenzene to yield compound 40 which is then reduced with $H_2$ and Pd/C under normal pressure to yield 6-amino-quinoline derivative 41. Acylation of the 6-amino group with a carboxyl chloride leads to carboxamide 42. Likewise reaction with a carbodiimide led to guanidines, with carbamoyl chlorides led to urea derivatives, with formic acid esters to carbamates and with sulfamoyl chlorides to sulfamides.

EXAMPLES

Where an example is said to be carried out in accordance with a general procedure described herein, it is understood that the reaction parameters may have been adjusted in accordance with the knowledge of those skilled in the art to achieve the recited compound.

Example 1

N2-(2-Phenoxy-ethyl)-N6-pyridin-3-ylmethyl-quinoline-2,6-diamine

Step A 2,6-Dichloroquinoline (1.0 g, 5.1 mmol) and 2-phenoxyethylamine (1.5 g, 11 mmol) were microwaved at 120° C. for 1 h. The reaction mixture was purified by flash chromatography on silica gel (cyclohexane/ethyl acetate 100:0->70:30 gradient). (6-Chloro-quinolin-2-yl)-(2-phenoxy-ethyl)-amine was obtained as a light yellow solid (1.1 g, 73%), MS: m/e=299.3 (M+H$^+$).

Step B (6-Chloro-quinolin-2-yl)-(2-phenoxy-ethyl)-amine (150 mg, 0.503 mmol) was dissolved in 2 mL dioxane. Argon was bubbled through the solution for 2 minutes to remove oxygen. 3-Picolylamine (165 mg, 1.53 mmol), sodium tert.-butylate (119 mg, 1.24 mmol) and 1,1'-2-(dimethylamino)ferrocen-1-yl-palladium(II) chloride dinorbornylphosphine (16 mg, 0.03 mmol) were added. The reaction mixture was stirred in a sealed tube at 115° C. for 16 h. The solvent was evaporated and the residue purified by flash chromatography on silica gel (dichloromethane/methanol 100:0->90:10 gradient). The title compound was obtained as a light brown solid (108 mg, 58%), MS: m/e=371.1 (M+H$^+$).

Example 2

(2-Methoxy-benzyl)-[6-((E)-2-pyridin-4-yl-vinyl)-quinolin-2-yl]-amine

Step A

6-Bromo-2 chloroquinoline (727 mg, 3.0 mmol) and 2-methoxybenzylamine (823 mg, 6.0 mmol were stirred in a sealed tube at 120° C. for 16 h. The reaction mixture was purified by flash chromatography on silica gel (cyclohexane/ethyl acetate 100:0->70:30 gradient). (6-Bromo-quinolin-2-yl)-(2-methoxy-benzyl)-amine was obtained as a light yellow solid (868 mg, 84%), MS: m/e=343.1 (M+H$^+$).

Step B (6-Bromo-quinolin-2-yl)-(2-methoxy-benzyl)-amine (200 mg, 0.583 mmol) was dissolved in 2 mL dimethylformamide. 4-Vinylpyridine (80 mg, 0.762 mmol), triethylamine (77 mg, 0.760 mmol), tri-o-tolylphosphin (7 mg, 0.023 mmol) and palladium(II)acetate (3 mg, 0.013 mmol) were added. The reaction mixture was stirred in a sealed tube at 100° C. for 16 h. The reaction mixture was poured into 30 mL water and extracted three times with ethyl acetate (30 mL each). The combined organic extracts were dried with sodium sulfate, filtered and evaporated. The residue purified by flash chromatography on silica gel (dichloromethane/methanol 100:0->90:10 gradient). The title compound was obtained as a light yellow solid (65 mg, 30%), MS: m/e=368.1 (M+H$^+$).

Example 3

(2-Methoxy-benzyl)-[6-(2-pyridin-4-yl-ethyl)-quinolin-2-yl]-amine (2-Methoxy-benzyl)-[6-((E)-2-pyridin-4-yl-vinyl)-quinolin-2-yl]-amine (example 2, 51 mg, 0.139 mmol) was dissolved in 20 mL ethanol. Palladium on charcoal (10%, 15 mg, 0.014 mmol) was added and the reaction mixture war hydrogenated with a hydrogen balloon overnight. The palladium was filtered off and the solvent was evaporated. The title compound was obtained as a yellow oil (40 mg, 78%), MS: m/e=370.1 (M+H$^+$).

Example 4

(2-Methoxy-benzyl)-(6-phenethyl-quinolin-2-yl)-amine

The title compound, MS: m/e=369.1 (M+H$^+$), was prepared in accordance with the general method of examples 2 and 3 from 6-bromo-2-chloroquinoline, 2-methoxybenzylamine and styrene.

Example 5

N2,N6-Bis-(2-phenoxy-ethyl)-quinoline-2,6-diamine

The title compound, MS: m/e=400.0 (M+H$^+$), was prepared in accordance with the general method of example 1 from 2,6-dichloroquinoline and 2-phenoxyethylamine.

Example 6

N2-(2-Methoxy-benzyl)-N6-pyridin-3-ylmethyl-quinoline-2,6-diamine

The title compound, MS: m/e=371.0 (M+H$^+$), was prepared in accordance with the general method of example 1 from 2,6-dichloroquinoline, 2-methoxybenzylamine and 3-(aminomethyl)pyridine.

Example 7

N2-(2-Phenoxy-ethyl)-N6-pyridin-4-ylmethyl-quinoline-2,6-diamine

The title compound, MS: m/e=371.1 (M+H$^+$), was prepared in accordance with the general method of example 1 from 2,6-dichloroquinoline, 2-phenoxyethylamine and 4-(aminomethyl)pyridine.

Example 8

N6-Benzyl-N2-(2-methoxy-benzyl)-quinoline-2,6-diamine

The title compound, MS: m/e=369.9 (M+H$^+$), was prepared in accordance with the general method of example 1 from 2,6-dichloroquinoline, 2-methoxybenzylamine and benzylamine.

Example 9

N6-(2-Methoxy-benzyl)-N2-(2-phenoxy-ethyl)-quinoline-2,6-diamine

The title compound, MS: m/e=400.3 (M+H$^+$), was prepared in accordance with the general method of example 1 from 2,6-dichloroquinoline, 2-phenoxyethylamine and 2-methoxybenzylamine.

Example 10

N6-(3-Methoxy-benzyl)-N2-(2-phenoxy-ethyl)-quinoline-2,6-diamine

The title compound, MS: m/e=400.4 (M+H$^+$), was prepared in accordance with the general method of example 1 from 2,6-dichloroquinoline, 2-phenoxyethylamine and 3-methoxybenzylamine.

Example 11

N6-(4-Methoxy-benzyl)-N2-(2-phenoxy-ethyl)-quinoline-2,6-diamine

The title compound, MS: m/e=400.1 (M+H$^+$), was prepared in accordance with the general method of example 1 from 2,6-dichloroquinoline, 2-phenoxyethylamine and 4-methoxybenzylamine.

Example 12

N6-Methyl-N2-(2-phenoxy-ethyl)-N6-pyridin-3-ylmethyl-quinoline-2,6-diamine

The title compound, MS: m/e=385.1 (M+H$^+$), was prepared in accordance with the general method of example 1 from 2,6-dichloroquinoline, 2-phenoxyethylamine and N-methyl-3-picolylamine.

Example 13

N2-(2-Methoxy-benzyl)-4-phenyl-N6-pyridin-3-ylmethyl-quinoline-2,6-diamine

Step A

6-Chloro-4-phenyl-quinolin-2-ylamine (CAS 51478-40-1, 750 mg, 2.94 mmol) was dissolved in 40 mL dichloromethane. 2-Methoxybenzaldehyde (481 mg, 3.54 mmol) and acetic acid (354 mg, 5.9 mmol) were added. The reaction mixture was stirred at room temperature for 2 h. Sodium triacetoxy borohydride (1.39 g, 6.59 mmol) was added and stirring was continued overnight. The reaction mixture was quenched by addition of 100 mL sat. sodiumbicarbonate solution. The mixture was extracted three times with dichloromethane (100 mL each). The organic phases ware pooled, dried with sodium sulfate, filtered and evaporated. The residue purified by flash chromatography on silica gel (cyclohexane/ethyl acetate 100:0->80:20 gradient). (6-Chloro-4-phenyl-quinolin-2-yl)-(2-methoxy-benzyl)-amine was obtained as an off-white solid (595 mg, 54%), MS: m/e=375.1 (M+H$^+$).

Step B

The title compound, MS: m/e=447.3 (M+H$^+$), was prepared in accordance with the general method of example 1 B from (6-chloro-4-phenyl-quinolin-2-yl)-(2-methoxy-benzyl)-amine and 3-picolylamine.

Example 14

(2-Methoxy-benzyl)-[6-((E)-2-pyridin-3-yl-vinyl)-quinolin-2-yl]-amine

Step A (6-Bromo-quinolin-2-yl)-(2-methoxy-benzyl)-amine (example 2, step A, 500 mg, 1.46 mmol) was dissolved in 20 mL toluene. The reaction mixture was evacuated and backfilled with argon for three times to remove oxygen. Vinyltributyltin (462 mg, 1.46 mmol) and tetrakis(triphenylphosphin)palladium(0) (34 mg, 0.029 mmol) were added. The reaction mixture was refluxed overnight and evaporated. The residue was poured into 50 mL acetonitrile and extracted three times with heptane (50 mL each) to remove the tin products. The acetonitrile phase was dried with sodium sulfate, filtered and evaporated. The residue was purified by flash chromatography on silica gel (cyclohexane/ethyl acetate 100:0->80:20 gradient). (2-Methoxy-benzyl)-(6-vinyl-quinolin-2-yl)-amine was obtained as a yellow oil (478 mg), MS: m/e=291.1 (M+H$^+$).

Step B (2-Methoxy-benzyl)-(6-vinyl-quinolin-2-yl)-amine (240 mg, 0.828 mmol) was reacted with 3-bromopyridine (170 mg, 1.08 mmol) as described in example 2 step B. The title compound was obtained as a yellow waxy solid (100 mg, 33%), MS: m/e=368.0 (M+H$^+$).

Example 15

N2,N6-Bis-(2-methoxy-benzyl)-quinoline-2,6-diamine

The title compound, MS: m/e=400.4 (M+H$^+$), was prepared in accordance with the general method of example 1 from 2,6-dichloroquinoline and 2-methoxybenzylamine.

Example 16

N6-(3-Methoxy-benzyl)-N2-(2-methoxy-benzyl)-quinoline-2,6-diamine

The title compound, MS: m/e=400.0 (M+H$^+$), was prepared in accordance with the general method of example 1 from 2,6-dichloroquinoline, 2-methoxybenzylamine and 3-methoxybenzylamine.

Example 17

N2-(2-Methoxy-benzyl)-N6-(2-trifluoromethoxy-benzyl)-quinoline-2,6-diamine

The title compound, MS: m/e=454.0 (M+H$^+$), was prepared in accordance with the general method of example 1 from 2,6-dichloroquinoline, 2-methoxybenzylamine and 2-(trifluoromethoxy)benzylamine.

Example 18

(2-Methoxy-benzyl)-[6-(2-pyridin-3-yl-ethyl)-quinolin-2-yl]-amine

The title compound, MS: m/e=370.0 (M+H$^+$), was prepared in accordance with the general method of example 3 from (2-methoxy-benzyl)-[6-((E)-2-pyridin-3-yl-vinyl)-quinolin-2-yl]-amine (example 14).

Example 19

N6-(3-Methoxy-benzyl)-N2-(2-methoxy-benzyl)-4-phenyl-quinoline-2,6-diamine

The title compound, MS: m/e=476.0 (M+H$^+$), was prepared in accordance with the general method of example 13 from 6-chloro-4-phenyl-quinolin-2-ylamine (CAS 51478-40), 2-methoxybenzaldehyde and 3-methoxybenzylamine.

Example 20

N2,N6-Bis-(2-methoxy-benzyl)-4-phenyl-quinoline-2,6-diamine

The title compound, MS: m/e=476.3 (M+H$^+$), was prepared in accordance with the general method of example 13 from 6-chloro-4-phenyl-quinolin-2-ylamine (CAS 51478-40), 2-methoxybenzaldehyde and 2-methoxybenzylamine.

Example 21

N2-(2-Methoxy-benzyl)-N6-(5-methyl-furan-2-ylmethyl)-quinoline-2,6-diamine

The title compound, MS: m/e=374.1 (M+H$^+$), was prepared in accordance with the general method of example 1 from 2,6-dichloroquinoline, 2-methoxybenzylamine and 5-methyl-2-furanmethanamine.

Example 22

N2-(2-Methoxy-benzyl)-N6-(3-methyl-3H-imidazol-4-ylmethyl)-quinoline-2,6-diamine

The title compound, MS: m/e=374.1 (M+H$^+$), was prepared in accordance with the general method of example 1 from 2,6-dichloroquinoline, 2-methoxybenzylamine and (1-methyl-1H-imidazol-5-yl)methylamine.

Example 23

N6-(3-Imidazol-1-yl-propyl)-N2-(2-methoxy-benzyl)-quinoline-2,6-diamine

The title compound, MS: m/e=388.4 (M+H$^+$), was prepared in accordance with the general method of example 1 from 2,6-dichloroquinoline, 2-methoxybenzylamine and 1-(3-aminopropyl)imidazole.

Example 24

(2-Methoxy-benzyl)-{6-[2-(2-methoxy-phenyl)-ethyl]-quinolin-2-yl}-amine

The title compound, MS: m/e=399.3 (M+H$^+$), was prepared in accordance with the general method of example 14 and 3 from 6-bromo-2-chloroquinoline, 2-methoxybenzylamine, vinyltributyltin and 2-bromoanisole.

Example 25

N2-(5-Methyl-furan-2-ylmethyl)-N6-pyridin-3-ylmethyl-quinoline-2,6-diamine

The title compound, MS: m/e=345.3 (M+H$^+$), was prepared in accordance with the general method of example 1 from 2,6-dichloroquinoline, 5-methyl-2-furanmethanamine and 3-picolylamine.

Example 26

N6-Pyridin-3-ylmethyl-N2-pyridin-2-ylmethyl-quinoline-2,6-diamine

The title compound, MS: m/e=342.1 (M+H$^+$), was prepared in accordance with the general method of example 1 from 2,6-dichloroquinoline, 2-picolylamine and 3-picolylamine.

Example 27

N6-(2-Methoxy-benzyl)-N2-(5-methyl-furan-2-ylmethyl)-quinoline-2,6-diamine

The title compound, MS: m/e=374.0 (M+H$^+$), was prepared in accordance with the general method of example 1 from 2,6-dichloroquinoline, 5-methyl-2-furanmethanamine and 2-methoxybenzylamine.

Example 28

N6-(3-Methoxy-benzyl)-N2-(5-methyl-furan-2-ylmethyl)-quinoline-2,6-diamine

The title compound, MS: m/e=374.3 (M+H$^+$), was prepared in accordance with the general method of example 1 from 2,6-dichloroquinoline, 5-methyl-2-furanmethanamine and 3-methoxybenzylamine.

Example 29

N6-Benzyl-N2-(5-methyl-furan-2-ylmethyl)-quinoline-2,6-diamine

The title compound, MS: m/e=344.1 (M+H$^+$), was prepared in accordance with the general method of example 1 from 2,6-dichloroquinoline, 5-methyl-2-furanmethanamine and benzylamine.

Example 30

N2-(2-Methoxy-benzyl)-4-pyridin-3-yl-N6-pyridin-3-ylmethyl-quinoline-2,6-diamine

Step A

2-Amino-6-chloro-4-hydroxyquinoline (CAS 64319-84-2, 6.0 g, 31 mmol) were added portionswise to phosphorus tribromide (25 g, 92 mmol). Phosphorus oxybromide (10 g, 37 mmol) were added and the mixture was stirred at 150° C. for 16 h. The mixture was poured into 300 mL ice water and the pH was adjusted to 11 by addition of 32% sodium hydroxide solution. The solid was filtered off and washed with water and cyclohexane. 4-Bromo-6-chloro-quinolin-2-ylamine was obtained as a yellow solid (7.8 g, 98%), MS: m/e=258.9 (M+H$^+$).

Step B

4-Bromo-6-chloro-quinolin-2-ylamine (3.12 g, 12 mmol) was dissolved in 100 mL 1,2-dichloroethane. 2-Methoxybenzaldehyde (1.98 g, 15 mmol) and acetic acid (2.91 g, 48 mmol) were added. The reaction mixture was stirred at 40° C. for 3 h. Sodium triacetoxy borohydride (5.99 g, 25 mmol) was added and stirring was continued at room temperature overnight. The reaction mixture was quenched by addition of 200 mL sat. sodiumbicarbonate solution. The mixture was extracted three times with dichloromethane (200 mL each).

The organic phases ware pooled, dried with sodium sulfate, filtered and evaporated. The residue purified by flash chromatography on silica gel (cyclohexane/ethyl acetate 100:0->80:20 gradient). (4-Bromo-6-chloro-quinolin-2-yl)-(2-methoxy-benzyl)-amine was obtained as an off-white solid (2.2 g, 48%), MS: m/e=379.1 (M+H$^+$).

Step C (4-Bromo-6-chloro-quinolin-2-yl)-(2-methoxy-benzyl)-amine (530 mg, 1.4 mmol) and pyridine-3-boronic acid (224 mg, 1.8 mmol) were dissolved in 16 mL dimethoxyethane and 8 mL 2N sodium carbonate solution. The reaction mixture was evacuated and backfilled with argon for three times. Triphenylphosphine (37 mg, 0.141 mmol) and palladium acetate (16 mg, 0.071 mmol) were added and the mixture was refluxed overnight. The mixture was extracted three times with ethyl acetate (200 mL each). The organic phases ware pooled, dried with sodium sulfate, filtered and evaporated. The residue purified by flash chromatography on silica gel (cyclohexane/ethyl acetate 100:0->30:70 gradient). (6-Chloro-4-pyridin-3-yl-quinolin-2-yl)-(2-methoxy-benzyl)-amine was obtained as a white foam (500 mg, 94%), MS: m/e=376.4 (M+H$^+$).

Step D (6-Chloro-4-pyridin-3-yl-quinolin-2-yl)-(2-methoxy-benzyl)-amine (185 mg, 0.492 mmol) was dissolved in 5 mL toluene and 1 mL tert. butanol. Argon was bubbled through the solution for 2 minutes to remove oxygen. 3-Picolylamine (160 mg, 1.48 mmol), sodium tert.-butylate (95 mg, 0.99 mmol), palladium acetate (6 mg, 0.027 mmol) and 2-dicyclohexyl-phosphino-2',4',6'-triisopropylbiphenyl (X-Phos, 23 mg, 0.05 mmol) were added. The reaction mixture was stirred in a sealed tube at 130° C. for 16 h. The solvent was evaporated and the residue purified by flash chromatography on silica gel (dichloromethane/methanol 100:0->90:10 gradient). The title compound was obtained as a yellow foam (105 mg, 47%), MS: m/e=448.3 (M+H$^+$).

Example 31

N-2-(4-Fluoro-2-methoxy-benzyl)-4-phenyl-N-6-pyridin-3-ylmethyl-quinoline-2,6-diamine The title compound, MS: m/e=465.4 (M+H$^+$), was prepared in accordance with the general method of example 13 from 6-chloro-4-phenyl-quinolin-2-ylamine (CAS 51478-40), 4-fluoro-2-methoxybenzaldehyde and 3-picolylamine.

Example 32

N2-(2-Methoxy-benzyl)-N6-pyridin-3-ylmethyl-4-o-tolyl-quinoline-2,6-diamine

The title compound, MS: m/e=461.5 (M+H$^+$), was prepared in accordance with the general method of example 30 from 2-amino-6-chloro-4-hydroxyquinoline (CAS 64319-84-2), o-tolyl-phenylboronic acid, 2-methoxybenzaldehyde and 3-picolylamine.

Example 33

N-2-(2-Methoxy-benzyl)-4-(3-methoxy-phenyl)-N-6-pyridin-3-ylmethyl-quinoline-2,6-diamine The title compound, MS: m/e=477.4 (M+H$^+$), was prepared in accordance with the general method of example 30 from 2-amino-6-chloro-4-hydroxyquinoline (CAS 64319-84-2), 3-methoxyphenylboronic acid, 2-methoxybenzaldehyde and 3-picolylamine.

Example 34

N-2,N-6-Bis-(2-methoxy-benzyl)-4-(3-methoxy-phenyl)-quinoline-2,6-diamine

The title compound, MS: m/e=506.4 (M+H$^+$), was prepared in accordance with the general method of example 30 from 2-amino-6-chloro-4-hydroxyquinoline (CAS 64319-84-2), 3-methoxyphenylboronic acid, 2-methoxybenzaldehyde and 2-methoxy-benzylamine.

Example 35

4-(2,5-Difluoro-phenyl)-N2-(2-methoxy-benzyl)-N6-pyridin-3-ylmethyl-quinoline-2,6-diamine The title compound, MS: m/e=483.5 (M+H$^+$), was prepared in accordance with the general method of example 30 from 2-amino-6-chloro-4-hydroxyquinoline (CAS 64319-84-2), 2,5-difluorophenylboronic acid, 2-methoxybenzaldehyde and 3-picolylamine.

Example 36

N-6-Benzyl-N-2-(4-fluoro-2-methoxy-benzyl)-4-phenyl-quinoline-2,6-diamine

The title compound, MS: m/e=464.1 (M+H$^+$), was prepared in accordance with the general method of example 13 from 6-chloro-4-phenyl-quinolin-2-ylamine (CAS 51478-40), 4-fluoro-2-methoxybenzaldehyde and benzylamine.

Example 37

N-2-(4-Fluoro-2-methoxy-benzyl)-4-phenyl-N-6-&-pyridin-4-ylmethyl-quinoline-2,6-diamine The title compound, MS: m/e=465.3 (M+H$^+$), was prepared in accordance with the general method of example 13 from 6-chloro-4-phenyl-quinolin-2-ylamine (CAS 51478-40), 4-fluoro-2-methoxybenzaldehyde and 4-picolylamine.

Example 38

N-6-2-Benzyl-N-2-(4-fluoro-2-methoxy-benzyl)-4-o-tolyl-quinoline-2,6-diamine

The title compound, MS: m/e=478.4 (M+H$^+$), was prepared in accordance with the general method of example 30 from 2-amino-6-chloro-4-hydroxyquinoline (CAS 64319-84-2), o-tolyl-phenylboronic acid, 4-fluoro-2-methoxybenzaldehyde and benzylamine.

Example 39

N-2-(4-Fluoro-2-methoxy-benzyl)-N-6-pyridin-4-ylmethyl-4-o-tolyl-quinoline-2,6-diamine The title compound, MS: m/e=479.3 (M+H$^+$), was prepared in accordance with the general method of example 30 from 2-amino-6-chloro-4-hydroxyquinoline (CAS 64319-

84-2), o-tolyl-phenylboronic acid, 4-fluoro-2-methoxybenzaldehyde and 4-picolylamine.

Example 40

N2-(4-Fluoro-2-methoxy-benzyl)-N4-(2-methoxy-ethyl)-N6-pyridin-3-ylmethyl-quinoline-2,4,6-triamine Step A (4-Bromo-6-chloro-quinolin-2-yl)-(4-fluoro-2-methoxy-benzyl)-amine (prepared from 2-amino-6-chloro-4-hydroxyquinoline and 4-fluoro-2-methoxybenzaldehyde as described in example 30, step A and B, 328 mg, 0.828 mmol) was dissolved in 5 mL dioxane. Argon was bubbled through the solution for 2 minutes to remove oxygen. 2-Methoxyethylamine (187 mg, 2.49 mmol), sodium tert.-butylate (159 mg, 1.66 mmol), 1,1'-bis(diphenylphosphino)ferrocene (69 mg, 0.125 mmol) and 1,1'-bis(diphenylphosphino)ferrocene palladium (II) chloride (34 mg, 0.042 mmol) were added. The reaction mixture was stirred in a sealed tube at 100° C. for 2 h. The solvent was evaporated and the residue purified by flash chromatography on silica gel (dichloromethane/methanol/ammonia 100:0:0->110:10:1 gradient). 6-Chloro-N2-(4-fluoro-2-methoxy-benzyl)-N4-(2-methoxy-ethyl)-quinoline-2,4-diamine was obtained as an off-white foam (285 mg, 88%), MS: m/e=390.0 (M+H$^+$).

Step B

The title compound, MS: m/e=462.5 (M+H$^+$), was prepared in accordance with the general method of example 30, step D from 6-chloro-N2-(4-fluoro-2-methoxy-benzyl)-N4-(2-methoxy-ethyl)-quinoline-2,4-diamine and 3-picolylamine.

Example 41

N2-(2-Methoxy-benzyl)-N6-(1-methyl-1H-imidazol-4-ylmethyl)-quinoline-2,6-diamine The title compound, MS: m/e=374.4 (M+H$^+$), was prepared in accordance with the general method of example 1 from 2,6-dichloroquinoline, 2-methoxybenzylamine and (1-methyl-1H-imidazol-4-yl)methylamine.

Example 42

N6-Benzyl-N2-(4-fluoro-2-methoxy-benzyl)-N4-(2-methoxy-ethyl)-quinoline-2,4,6-triamine The title compound, MS: m/e=461.1 (M+H$^+$), was prepared in accordance with the general method of example 40 from (4-bromo-6-chloro-quinolin-2-yl)-(4-fluoro-2-methoxy-benzyl)-amine, methoxyethylamine and benzylamine.

Example 43

(2-Methoxy-benzyl)-(6-phenoxymethyl-quinolin-2-yl)-amine

Step A (6-Bromo-quinolin-2-yl)-(2-methoxy-benzyl)-amine was prepared from 6-bromo-2-chloroquinoline and 2-methoxybenzylamine as described in example 2 step A.

Step B (6-Bromo-quinolin-2-yl)-(2-methoxy-benzyl)-amine (2.0 g, 5.83 mmol) was dissolved in 100 mL tetrahydrofurane. n-Butyllithium solution (1.6 M in hexane, 9.1 mL, 14.6 mmol) was slowly added at −78° C. The reaction mixture was allowed to warm to −10° C. and stirred at this temperature for 45 min. The reaction mixture was then cooled again to −78° C. and dimethylformamide (1.07 g, 14.6 mmol) was added. The mixture was then slowly warmed up and quenched with 200 mL water at 5° C. The solvent was evaporated off. The residue was extracted three times with ethyl acetate (200 mL each). The organic phases ware pooled, dried with sodium sulfate, filtered and evaporated. The residue was purified by flash chromatography on silica gel (cyclohexane/ethyl acetate 100:0->50:50 gradient). 2-(2-Methoxy-benzylamino)-quinoline-6-carbaldehyde was obtained as a light yellow solid (683 mg, 40%), MS: m/e=293.1 (M+H$^+$).

Step C 2-(2-Methoxy-benzylamino)-quinoline-6-carbaldehyde (663 mg, 2.27 mmol) was dissolved in 25 mL methanol and sodium borohydride (343 mg, 9.03 mmol) was added. The reaction mixture was refluxed for 3 h. The solvent was evaporated off. The residue was taken up in 100 mL water and extracted three times with ethyl acetate (100 mL each). The organic phases ware pooled, dried with sodium sulfate, filtered and evaporated. The crude product was recrystallized from dichloromethane. [2-(2-Methoxy-benzylamino)-quinolin-6-yl]-methanol was obtained as a white solid (369 mg, 59%), MS: m/e=295.3 (M+H$^+$).

Step D

[2-(2-Methoxy-benzylamino)-quinolin-6-yl]-methanol (200 mg, 0.680 mmol) was dissolved in 13 mL tetrahydrofurane. Phenol (70 mg, 0.745 mmol) and triphenylphosphine (200 mg, 0.763 mmol) were added at room temperature. Diisopropyl azodicarboxylate (159 mg, 0.787 mmol) was slowly added at 0° C. The reaction mixture was stirred at room temperature overnight. The reaction mixture was quenched by addition of 50 mL 2N sodium carbonate. The mixture was extracted three times with dichloromethane (50 mL each). The organic phases ware pooled, dried with sodium sulfate, filtered and evaporated. The residue was purified by flash chromatography on silica gel (cyclohexane/ethyl acetate 100:0->50:50 gradient). The title compound was obtained as an off-white solid (105 mg, 41%), MS: m/e=371.4 (M+H$^+$).

Example 44

N6-Benzyl-N2-(4-fluoro-2-methoxy-benzyl)-quinoline-2,4,6-triamine

N4-Allyl-6-chloro —N2-(4-fluoro-2-methoxy-benzyl)-quinoline-2,4-diamine (prepared from (4-bromo-6-chloro-quinolin-2-yl)-(4-fluoro-2-methoxy-benzyl)-amine and allylamine as described in example 40, step A) was coupled with benzylamine as described in example 30, step D. The title compound was obtained as a light brown foam (16%), MS: m/e=403.4 (M+H$^+$).

Example 45

N2-(2-Methoxy-benzyl)-N6-(2-methoxymethyl-benzyl)-quinoline-2,6-diamine

The title compound, MS: m/e=414.1 (M+H$^+$), was prepared in accordance with the general method of example 1 from 2,6-dichloroquinoline, 2-methoxybenzylamine and 3-methoxymethyl-benzylamine (CAS 148278-90-4).

Example 46

N2-(4-Fluoro-2-methoxy-benzyl)-N6-(2-methoxy-benzyl)-quinoline-2,4,6-triamine

The title compound, MS: m/e=433.2 (M+H$^+$), was prepared in accordance with the general method of example 44 from N4-allyl-6-chloro-N2-(4-fluoro-2-methoxy-benzyl)-quinoline-2,4-diamine and 2-methoxybenzylamine

Example 47

N6-Benzyl-N2-(2-methoxy-benzyl)-quinoline-2,4,6-triamine

The title compound, MS: m/e=385.3 (M+H$^+$), was prepared in accordance with the general method of example 44 from N4-allyl-6-chloro-N2-(2-methoxy-benzyl)-quinoline-2,4-diamine and benzylamine

Example 48

N2,N6-Bis-(2-methoxy-benzyl)-quinoline-2,4,6-triamine

The title compound, MS: m/e=415.5 (M+H$^+$), was prepared in accordance with the general method of example 44 from N4-allyl-6-chloro-N2-(2-methoxy-benzyl)-quinoline-2,4-diamine and 2-methoxybenzylamine

Example 49

(5-Methyl-furan-2-ylmethyl)-[6-(pyridin-3-ylaminomethyl)-quinolin-2-yl]-amine (5-Methyl-furan-2-ylmethyl)-[6-(pyridin-3-ylaminomethyl)-quinolin-2-yl]-amine (prepared from 6-bromo-2-chloro-quinoline, 5-methyl-2-furanmethanamine and dimethylformamide as described in example 43, step A and B, 200 mg, 0.752 mmol) was dissolved in 5 mL dichloromethane. 3-Aminopyridine (85 mg, 0.904 mmol) and acetic acid (90 mg, 1.50 mmol) were added. The reaction mixture was stirred at room temperature for 1 h. Sodium triacetoxy borohydride (318 mg, 1.5 mmol) was added and stirring was continued overnight. The reaction mixture was quenched by addition of 50 mL water. The mixture was extracted three times with dichloromethane (50 mL each). The organic phases ware pooled, dried with sodium sulfate, filtered and evaporated. The residue was purified by flash chromatography on silica gel (dichloromethane/methanol 100:0->90:10 gradient). The title compound was obtained as an off-white solid (55 mg, 21%), MS: m/e=345.1 (M+H$^+$).

Example 50

(5-Methyl-furan-2-ylmethyl)-(6-phenylaminomethyl-quinolin-2-yl)-amine

The title compound, MS: m/e=344.3 (M+H$^+$), was prepared in accordance with the general method of example 49 from (5-methyl-furan-2-ylmethyl)-[6-(pyridin-3-ylaminomethyl)-quinolin-2-yl]-amine and aniline.

Example 51

N2-(2-Methoxy-benzyl)-N6-pyridin-3-ylmethyl-quinoline-2,4,6-triamine

The title compound, MS: m/e=386.4 (M+H$^+$), was prepared in accordance with the general method of example 44 from N4-allyl-6-chloro-N2-(2-methoxy-benzyl)-quinoline-2,4-diamine and 3-picolylamine

Example 52

N2-(2-Methoxy-benzyl)-N6-[3-(2-methoxy-ethoxymethyl)-benzyl]-quinoline-2,6-diamine The title compound, MS: m/e=458.5 (M+H$^+$), was prepared in accordance with the general method of example 1 from 2,6-dichloroquinoline, 2-methoxybenzylamine and 3-(2-methoxy-ethoxymethyl)-benzylamine.

Synthesis of 3-(2-methoxy-ethoxymethyl)-benzylamine

Step 1

Sodium hydride (55% in mineral oil, 1.76 g, 40.5 mmol) was suspended in 100 mL tetrahydrofurane. 3-(Hydroxymethyl)benzonitrile (5.0 g, 36.5 mmol), dissolved in 200 mL tetrahydrofuran was added drop wise. The reaction mixture was stirred at room temperature for 1 h. 2-Bromoethylmethylether (7.0 mL, 76 mmol) was added and the reaction mixture was refluxed overnight. The reaction mixture was quenched with 3 mL 2N sodium carbonate solution and the solvent was evaporated. The residue was taken up in 100 mL water and extracted three times with ethyl acetate (100 mL each). The organic phases ware pooled, dried with sodium sulfate, filtered and evaporated. The residue was purified by flash chromatography on silica gel (cyclohexane/ethyl acetate 100:0->50:50 gradient). 3-(2-Methoxy-ethoxymethyl)-benzonitrile was obtained as a yellow liquid (2.63 g, 38%).

Step 2

3-(2-Methoxy-ethoxymethyl)-benzonitrile (2.58 g, 13.5 mmol) was dissolved in 50 mL tetrahydrofuran. Lithiumaluminium hydride (660 mg, 17.5 mmol) was added portionwise at 0° C. The reaction mixture was stirred at room temperature overnight and quenched by sequential addition of 0.66 mL water, 0.66 mL 15% sodium hydroxide solution and 1.98 mL water. The solid was filtered off and the filtrate was evaporated. The title compound was obtained as a yellow liquid (2.63 g, 97%), MS: m/e=196.3 (M+H$^+$).

Example 53

N2-(2-Methoxy-benzyl)-N6-[3-(2-methoxy-ethoxy)-benzyl]-quinoline-2,6-diamine

The title compound, MS: m/e=444.4 (M+H$^+$), was prepared in accordance with the general method of example 1 from 2,6-dichloroquinoline, 2-methoxybenzylamine and 3-(2-methoxy-ethoxy)-benzonitrile (CAS 80407-67-6).

Example 54

N2-(5-Methyl-furan-2-ylmethyl)-N6-pyridin-3-ylmethyl-quinoline-2,4,6-triamine

The title compound, MS: m/e=360.2 (M+H$^+$), was prepared in accordance with the general method of example 44 from N4-allyl-6-chloro-N2-(5-methyl-furan-2-ylmethyl)-quinoline-2,4-diamine and 3-picolylamine.

Example 55

N6-Benzyl-N2-(5-methyl-furan-2-ylmethyl)-quinoline-2,4,6-triamine

The title compound, MS: m/e=359.2 (M+H$^+$), was prepared in accordance with the general method of example 44 from N4-allyl-6-chloro-N2-(5-methyl-furan-2-ylmethyl)-quinoline-2,4-diamine and benzylamine.

Example 56

N6-Benzyl-N2-(3-methoxy-benzyl)-quinoline-2,6-diamine

The title compound, MS: m/e=370.0 (M+H$^+$), was prepared in accordance with the general method of example 1 from 2,6-dichloroquinoline, 3-methoxybenzylamine and benzylamine.

Example 57

N2-(3-Methoxy-benzyl)-N6-pyridin-3-ylmethyl-quinoline-2,6-diamine

The title compound, MS: m/e=371.4 (M+H$^+$), was prepared in accordance with the general method of example 1 from 2,6-dichloroquinoline, 3-methoxybenzylamine and 3-picolylamine.

Example 58

N2-(3-Fluoro-benzyl)-N6-pyridin-3-ylmethyl-quinoline-2,6-diamine

The title compound, MS: m/e=359.1 (M+H$^+$), was prepared in accordance with the general method of example 1 from 2,6-dichloroquinoline, 3-fluorobenzylamine and 3-picolylamine.

Example 59

N6-Benzyl-N2-(3-fluoro-benzyl)-quinoline-2,6-diamine

The title compound, MS: m/e=358.1 (M+H$^+$), was prepared in accordance with the general method of example 1 from 2,6-dichloroquinoline, 3-fluorobenzylamine and benzylamine.

Example 60

N2-(3-Fluoro-benzyl)-N6-(3-trifluoromethyl-phenyl)-quinoline-2,6-diamine

The title compound, MS: m/e=412.3 (M+H$^+$), was prepared in accordance with the general method of example 1 from 2,6-dichloroquinoline, 3-fluorobenzylamine and 3-aminobenzotrifluoride.

Example 61

N-{2-[(5-Methyl-furan-2-ylmethyl)-amino]-quinolin-6-yl}-benzamide (6-Bromo-quinolin-2-yl)-(5-methyl-furan-2-ylmethyl)-amine (prepared from 6-bromo-2-chloroquinoline and 5-methyl-2-furanmethanamine as described in example 43, step A, 200 mg, 0.631 mmol) was dissolved in 5 mL dioxane. Argon was bubbled through the solution for 2 minutes to remove oxygen. Benzamide (107 mg, 0.884 mmol), cesium carbonate (308 mg, 0.948 mmol) bis(dibenzylideneacetone)palladium (29 mg, 0.032 mmol) and 4,5-bis(diphenylphosphino)-9,9-dimethylxanthene (55 mg, 0.095 mmol) were added. The reaction mixture was stirred in a sealed tube at 100° C. for 16 h. The solvent was evaporated and the residue purified by flash chromatography on silica gel (heptane/ethyl acetate 100:0->60:40 gradient). The title compound was obtained as a white solid (110 mg, 49%), MS: m/e=358.3 (M+H$^+$).

Example 62

(5-Methyl-furan-2-ylmethyl)-[6-((E)-2-pyridin-2-yl-vinyl)-quinolin-2-yl]-amine

The title compound, MS: m/e=342.3 (M+H$^+$), was prepared in accordance with the general method of example 2 from 6-bromo-2-chloroquinoline, 5-methyl-2-furanmethanamine and 2-vinylpyridine.

Example 63

N2-(5-Methyl-furan-2-ylmethyl)-N6-(2-trifluoromethoxy-benzyl)-quinoline-2,6-diamine The title compound, MS: m/e=428.1 (M+H$^+$), was prepared in accordance with the general method of example 1 from 2,6-dichloroquinoline, 5-methyl-2-furanmethanamine and 2-(trifluoromethoxy)benzylamine.

Example 64

N2-(5-Methyl-furan-2-ylmethyl)-N6-pyridin-4-ylmethyl-quinoline-2,6-diamine

The title compound, MS: m/e=345.1 (M+H$^+$), was prepared in accordance with the general method of example 1 from 2,6-dichloroquinoline, 5-methyl-2-furanmethanamine and 4-(aminomethyl)pyridine.

Example 65

(5-Methyl-furan-2-ylmethyl)-[6-(2-pyridin-2-yl-ethyl)-quinolin-2-yl]-amine

The title compound, MS: m/e=344.0 (M+H$^+$), was prepared in accordance with the general method of example 3 from (5-methyl-furan-2-ylmethyl)-[6-((E)-2-pyridin-2-yl-vinyl)-quinolin-2-yl]-amine (example 63).

Example 66

N6-Benzyl-N2-(5-fluoro-2-methoxy-benzyl)-quinoline-2,4,6-triamine

The title compound, MS: m/e=403.5 (M+H$^+$), was prepared in accordance with the general method of example 44 from N4-allyl-6-chloro-N2-(5-fluoro-2-methoxy-benzyl)-quinoline-2,4-diamine and benzylamine

Example 67

N6-Pyridin-3-ylmethyl-N2-(3-trifluoromethyl-phenyl)-quinoline-2,6-diamine

The title compound, MS: m/e=395.1 (M+H$^+$), was prepared in accordance with the general method of example 1 from 2,6-dichloroquinoline, (3-trifluoromethyl)aniline and 3-(aminomethyl)pyridine.

Example 68

N2-(5-Fluoro-2-methoxy-benzyl)-N6-pyridin-3-ylmethyl-quinoline-2,4,6-triamine

The title compound, MS: m/e=404.5 (M+H$^+$), was prepared in accordance with the general method of example 44 from N4-allyl-6-chloro-N2-(5-fluoro-2-methoxy-benzyl)-quinoline-2,4-diamine and 3-picolylamine

Example 69

N2-(5-Fluoro-2-methoxy-benzyl)-N6-pyridin-3-ylmethyl-quinoline-2,6-diamine

Step A

N6-Pyridin-3-ylmethyl-quinoline-2,6-diamine MS: m/e=251.5 (M+H$^+$), was prepared in accordance with the general method of example 1 from 2,6-dichloroquinoline, allylamine and 3-(aminomethyl)pyridine. The allyl protecting group was lost in the palladium catalyzed substitution reaction.

Step B

N6-Pyridin-3-ylmethyl-quinoline-2,6-diamine (150 mg, 0.6 mmol) was dissolved in 10 mL dichloromethane. 5-Fluoro-2-methoxybenzaldehyde (111 mg, 0.72 mmol) and acetic acid (72 mg, 1.2 mmol) were added. The reaction mixture was stirred at 40° C. for 3 h. Sodium triacetoxyborohydride (254 mg, 1.2 mmol) was added and stirring was continued at room temperature overnight. The reaction mixture was quenched by addition of 20 mL sat. sodiumbicarbonate solution. The mixture was extracted three times with dichloromethane (20 mL each). The organic phases ware pooled, dried with sodium sulfate, filtered and evaporated. The residue purified by flash chromatography on silica gel (dichloromethane/methanol 100:0->90:10 gradient). The title compound was obtained as a yellow gum (17 mg, 7%), MS: m/e=389.3 (M+H$^+$).

Example 70

N2-(5-Methyl-furan-2-ylmethyl)-N6-(3-trifluoromethyl-phenyl)-quinoline-2,6-diamine The title compound, MS: m/e=398.3 (M+H$^+$), was prepared in accordance with the general method of example 1 from 2,6-dichloroquinoline, 5-methyl-2-furanmethanamine and 3-(trifluoromethyl)aniline.

Example 71

N6-(4-Fluoro-phenyl)-N2-(5-methyl-furan-2-ylmethyl)-quinoline-2,6-diamine

The title compound, MS: m/e=348.3 (M+H$^+$), was prepared in accordance with the general method of example 1 from 2,6-dichloroquinoline, 5-methyl-2-furanmethanamine and 4-fluoroaniline.

Example 72

N2-(5-Methyl-furan-2-ylmethyl)-N6-pyridin-3-yl-quinoline-2,6-diamine

The title compound, MS: m/e=331.3 (M+H$^+$), was prepared in accordance with the general method of example 1 from 2,6-dichloroquinoline, 5-methyl-2-furanmethanamine and 3-aminopyridine.

Example 73

N2-Benzo[1,3]dioxol-4-ylmethyl-N6-pyridin-3-ylmethyl-quinoline-2,6-diamine

The title compound, MS: m/e=385.3 (M+H$^+$), was prepared in accordance with the general method of example 69 from 2,6-dichloroquinoline, 3-picolylamine and 2,3-(methylenedioxy)benzaldehyde.

Example 74

(2-Methoxy-benzyl)-[6-(3-methoxy-benzyloxy)-quinolin-2-yl]-amine

Step A

2-Chloro-6-hydroxy-quinoline (CAS RN 577967-89-6, 0.6 g, 3 mMol) and 3-methoxybenzylbromid (0.56 mL, 0.004 Mol) were dissolved in a slurry of potassium carbonate (0.55 g, 4 mMol) in 15 mL acetone and heated to reflux for 3 hr. Then water was added and the mixture extracted with ethyl acetate (3×20 mL). The combined organic phases were dried on sodium sulfate, filtered and evaporated. The residue was subjected to column chromatography on silica gel (heptane/ethyl acetate 10:0→9:1→4:1 gradient) to yield 2-chloro-6-(3-methoxy-benzyloxy)-quinoline (0.40 g, 40%) as a colorless solid; MS: m/e=300.3 (M+H$^+$).

Step B

The title compound was prepared according to the general method described in step A of example 2 from 2-chloro-6-(3-methoxy-benzyloxy)-quinoline and 3-methoxy-benzylbromide as a yellow oil (0.029 g, 27%); MS: m/e=400.3 (M+H$^+$).

Example 75

(2-Methoxy-benzyl)-[6-(pyridin-3-ylmethoxy)-quinolin-2-yl]-amine

The title compound, MS: m/e=372.3 (M+H$^+$), was prepared in accordance with the general method of example 74 from 2-chloro-6-hydroxy-quinoline, 3-pyridyl-benzyl bromide and 3-methoxy-benzylamine.

Example 76

2-(2-Methoxy-benzylamino)-quinoline-6-carboxylic acid 2-methoxy-benzylamide

A stirred mixture of 2-chloro-quinoline-6-carboxylic acid ethyl ester [CAS-No. 29969-56-0] (236 mg, 1.0 mmol) and commercially available 2-methoxy-benzylamine (412 mg, 3.0 mmol) was heated in a sealed tube for 16 h at 120° C. Purification by flash chromatography on silica gel (ethyl acetate/heptane) and crystallization of each of the two fractions (dichloromethane/hexane) yielded the title compound as a white solid (40 mg, 9%), MS (ISP) 428.3 [(M+H)$^+$]; m.p. 217° C. as well as 2-(2-methoxy-benzylamino)-quinoline-6-carboxylic acid ethyl ester as a white solid (196 mg, 58%), MS (ISP) 337.3 [(M+H)$^+$]; m.p. 108° C.

Example 77

4-Methoxy-N-[2-(2-methoxy-benzylamino)-quinolin-6-yl]-benzamide

Step A

2-Chloro-6-nitro-quinoline (0.80 g, 4.0 mmol) and 2-methoxybenzylamine (1.5 mL, 12 mmol) were heated at 130° C. for 2 h. The reaction mixture was purified by flash chromatography on silica gel (heptane/ethyl acetate, 9:1, 4:1, 1:1). (2-Methoxy-benzyl)-(6-nitro-quinolin-2-yl)-amine was obtained as a yellow solid (0.5 g, 42%), MS: m/e=310.5 (M+H$^+$).

Step B (2-Methoxy-benzyl)-(6-nitro-quinolin-2-yl)-amine (0.5 g, 2.0 mmol) were dissolved in ethyl acetate (25 ml). Upon addition of Pd/C (10%, 0.1 g) the reaction mixture was stirred for 45 min at ambient temperature under an atmosphere of hydrogen. Then the catalyst was filtered off, the filter washed with ethyl acetate and the filtrate evaporated. N-2-(2-Methoxy-benzyl)-quinoline-2,6-diamine was obtained as a yellow foam (0.40 g, 87%); MS: m/e=280.5 (M+H$^+$).

Step C

N-2-(2-Methoxy-benzyl)-quinoline-2,6-diamine (40 mg, 0.14 mmol) and p-anisoyl chloride (0.022 mL, 0.16 mmol) were dissolved in toluene (2 mL). The reaction mixture was heated to 50° C. for 3 h. Then the solvent was removed and the residue subjected to column chromatography (silica gel, heptane/ethyl acetate, 4:1, 1:1, 1:2). The title compound (15 mg, 25%) was obtained as a yellow solid; MS: m/e=414.7 (M+H$^+$).

Example 78

N-[2-(2-Methoxy-benzylamino)-quinolin-6-yl]-N,N-di-p-tolyl-guanidine

N-2-(2-Methoxy-benzyl)-quinoline-2,6-diamine (40 mg, 0.14 mmol) and 1,3-di-p-tolylcarbodiimid (0.035 mg, 0.16 mmol) were dissolved in toluene (2 mL). The reaction mixture was heated to 100° C. for 7 h. Then the solvent was removed and the residue subjected to column chromatography (silica gel, heptane/ethyl acetate, 4:1, 1:1, 0:1). The title compound (10 mg, 14%) was obtained as a yellow solid; MS: m/e=502.7 (M+H$^+$).

Example 79

1-[2-(2-Methoxy-benzylamino)-quinolin-6-yl]-3-(4-methoxy-phenyl)-urea

N-2-(2-Methoxy-benzyl)-quinoline-2,6-diamine (40 mg, 0.14 mmol) and 4-methoxyphenyl isocyanat (0.021 mg, 0.14 mmol) were dissolved in toluene (1 mL). The reaction mixture was heated to 60° C. for 16 h. Then the solvent was removed and a precipitate formed which was filtered, washed with toluene and dried under high vacuum. The title compound (21 mg, 34%) was obtained as a grey solid; MS: m/e=429.7 (M+H$^+$).

Example 80

[2-(2-Methoxy-benzylamino)-quinolin-6-yl]-carbamic acid 4-methoxy-phenyl ester

N-2-(2-Methoxy-benzyl)-quinoline-2,6-diamine (50 mg, 0.18 mmol), triethylamine (0.030 mL, 0.22 mmol) and 4-methoxyphenylchloroformat (0.027 mL, 0.18 mmol) were dissolved in toluene (3 mL). The reaction mixture was heated to 90° C. for 6 h. Then the solvent was removed and the residue subjected to column chromatography (silica gel, heptane/ethyl acetate, 9:1, 4:1, 1:1, 1:2). The title compound (15 mg, 20%) was obtained as an off-white solid; MS: m/e=430.7 (M+H$^+$).

Example 81

N-(4-fluorophenyl)-N'-{2-[(2-methoxybenzyl)amino]quinolin-6-yl}sulfamide

N-2-(2-Methoxy-benzyl)-quinoline-2,6-diamine (40 mg, 0.14 mmol) and 4-fluorphenylsulfamoylchloride (0.039 mg, 0.18 mmol) were dissolved in pyridine (1 mL). The reaction mixture was heated to 90° C. for 6 h. Then the solvent was removed and the residue subjected to column chromatography (silica gel, heptane/ethyl acetate, 9:1, 4:1, 1:1, 1:2). The title compound (12 mg, 19%) was obtained as a yellow foam; MS: m/e=453.7 (M+H$^+$).

Example 82

4-Fluoro-N-[2-(2-methoxy-benzylamino)-quinolin-6-ylmethyl]-benzamide

Step A

A mixture of (6-bromo-quinolin-2-yl)-(2-methoxy-benzyl)-amine (see example 2, step A) (500 mg, 1.46 mmol), zinc cyanide (188 mg, 1.6 mmol) and tetrakis-(triphenylphosphine)-palladium (168 mg, 0.145 mmol) in DMF (5 ml) was heated at 160° C. for 15 min in a microwave reactor. The reaction mixture was poured into water (30 ml) and extracted with diethyl ether (2×50 ml). The combined organic layers were washed with brine (2×30 ml), dried (MgSO$_4$) and evaporated. The crude product was purified by flash chromatography (ethyl acetate/heptane) on silica gel to yield 2-(2-methoxy-benzylamino)-quinoline-6-carbonitrile as light red oil (400 mg, 95%).

MS: m/e=290.1 (M+H$^+$).

Step B

Hydrogenation of 2-(2-methoxy-benzylamino)-quinoline-6-carbonitrile (395 mg, 1.365 mmol) dissolved in MeOH (20 ml) and 7N MeOH—NH$_3$ (10 ml) on R$^a$—Ni (395 mg) for 17 h at room temperature yielded after removal of the catalyst by filtration and evaporation a yellow oil which was further purified by flash chromatography (dichloromethane/MeOH/NH$_4$OH 15:1:0.1) on silica gel to yield (6-aminomethyl-quinolin-2-yl)-(2-methoxy-benzyl)-amine as colorless oil (400 mg, 100%).

MS: m/e=294.2 (M+H$^+$).

Step C

To a cooled (ice bath) and stirred solution of (6-aminomethyl-quinolin-2-yl)-(2-methoxy-benzyl)-amine (200 mg, 0.68 mmol) and triethyl amine (75 mg, 0.76 mmol) in THF (4 ml) was added 4-fluorobenzoyl chloride (119 mg, 0.75 mmol) and the mixture was allowed to stir at room temperature for 16 h. The reaction mixture was poured into water (15 ml) and extracted with diethyl acetate (2×20 ml). The combined organic layers were washed with brine (1×20 ml), dried (MgSO$_4$) and evaporated. The crude product was purified by flash chromatography (ethyl acetate/heptane) on silica gel and crystallization (dichloromethane/hexane) to yield the title compound as white foam (250 mg, 88%).
MS: m/e=416.4 (M+H$^+$).

Example 83

{6-[(4-Fluoro-benzylamino)-methyl]-quinolin-2-yl}-(2-methoxy-benzyl)-amine

A solution of (6-aminomethyl-quinolin-2-yl)-(2-methoxy-benzyl)-amine (example 85, step B) (390 mg, 1.33 mmol), 4-fluorobenzaldehyde (181.5 mg, 1.46 mmol) and acetic acid (319.3 mg, 5.32 mmol) in 1,2-dichloroethane (15 ml) was stirred at room temperature for 30 min. Afterwards sodium triacetoxy-boron hydride (657 mg, 2.79 mmol) was added, the reaction mixture was allowed to stir for 60 h at room temperature, poured into ice/saturated NaHCO$_3$ solution (30 ml) and extracted with dichloromethane (2×40 ml). The combined organic layers were washed with brine (30 ml), dried (MgSO$_4$) and evaporated. The crude product was purified by flash chromatography (ethyl acetate/heptane) on silica gel to yield the title compound as colorless oil (284 mg, 53%).
MS: m/e=402.5 (M+H$^+$).

Example 84

N2-(2-Methoxy-benzyl)-N6-pyrimidin-2-yl-quinoline-2,6-diamine

A mixture of (6-bromo-quinolin-2-yl)-(2-methoxy-benzyl)-amine (see example 2, step A) (171.6 mg, 0.5 mmol), commercially available 2-amino-pyrimidine (95.1 mg, 1.0 mmol), tert.-butyl-XPhos (34 mg, 0.08 mmol), Pd$_2$dba$_3$ (18.3 mg, 0.02 mmol), sodium tet.-butylate (52.9 mg, 0.55 mmol) and dioxane (3 ml) was heated in a sealed tube at 100° C. for 17 h. The reaction mixture was poured into water (20 ml) and extracted with ethyl acetate (2×40 ml). The combined organic layers were washed with brine (20 ml), dried (MgSO$_4$) and evaporated. Further purification of the crude product by flash chromatography on silica gel (ethyl acetate/heptane) and crystallization (dichloromethane/hexane) yielded the title compound (65 mg, 36%) as a light yellow solid.
MS: m/e=358.3 (M+H$^+$); m.p. 175° C.

Example 85

N2-(2-Methoxy-benzyl)-N6-(5-methyl-[1,3,4]oxadiazol-2-yl)-quinoline-2,6-diamine

The title compound, off-white solid, MS: m/e=362.3 (M+H$^+$); m.p. 183° C., was prepared in accordance with the general method of example 84 from (6-bromo-quinolin-2-yl)-(2-methoxy-benzyl)-amine (see example 2, step A) and commercially available 5-methyl-1,3,4-oxadiazol-2-yl-amine.

Example 86

N2-(2-Methoxy-benzyl)-N6-(3-methyl-[1,2,4]oxadiazol-5-yl)-quinoline-2,6-diamine

The title compound, light brown solid, MS: m/e=362.3 (M+H$^+$); m.p. 175° C., was prepared in accordance with the general method of example 84 from (6-bromo-quinolin-2-yl)-(2-methoxy-benzyl)-amine (see example 2, step A) and commercially available 3-methyl-1,2,4-oxadiazole-5-yl-amine [CAS-No. 3663-39-6].

Example 87

N6-(2-Ethyl-2H-tetrazol-5-yl)-N2-(2-methoxy-benzyl)-quinoline-2,6-diamine

The title compound, white solid, MS: m/e=376.4 (M+H$^+$); m.p. 190° C., was prepared in accordance with the general method of example 84 from (6-bromo-quinolin-2-yl)-(2-methoxy-benzyl)-amine (see example 2, step A) and commercially available 2-ethyl-2H-tetrazole-5-yl-amine.

Example 88

N2-(2-Methoxy-benzyl)-N6-(5-methyl-isoxazol-3-yl)-quinoline-2,6-diamine

The title compound, light yellow solid, MS: m/e=361.3 (M+H$^+$); m.p. 132° C., was prepared in accordance with the general method of example 84 from (6-bromo-quinolin-2-yl)-(2-methoxy-benzyl)-amine (see example 2, step A) and commercially available 5-methyl-isoxazole-3-yl-amine.

Example 89

N6-(4,6-Dimethyl-pyrimidin-2-yl)-N2-(2-methoxy-benzyl)-quinoline-2,6-diamine

The title compound, off-white solid, MS: m/e=386.2 (M+H$^+$); m.p. 157.5° C., was prepared in accordance with the general method of example 84 from (6-bromo-quinolin-2-yl)-(2-methoxy-benzyl)-amine (see example 2, step A) and commercially available 2-amino-4,6-dimethyl-pyrimidine.

Example 90

N2-(2-Methoxy-benzyl)-N6-(4-methyl-pyrimidin-2-yl)-quinoline-2,6-diamine

The title compound, off-white solid, MS: m/e=372.2 (M+H$^+$); m.p. 125° C., was prepared in accordance with the general method of example 84 from (6-bromo-quinolin-2-yl)-(2-methoxy-benzyl)-amine (see example 2, step A) and commercially available 2-amino-4-methyl-pyrimidine.

Example 91

N2-(2-Methoxy-benzyl)-N6-(3-methyl-pyridin-2-yl)-quinoline-2,6-diamine

The title compound, light yellow solid, MS: m/e=371.2 (M+H$^+$); m.p. 163° C., was prepared in accordance with the general method of example 84 from (6-bromo-quinolin-2-yl)-(2-methoxy-benzyl)-amine (see example 2, step A) and commercially available 2-amino-3-methyl-pyridine.

Example 92

N2-(2-Methoxy-benzyl)-N6-pyridin-2-yl-quinoline-2,6-diamine

The title compound, light brown solid, MS: m/e=357.2 (M+H$^+$); m.p. 134° C., was prepared in accordance with the

Example 93

N2-(2-Methoxy-benzyl)-N6-(6-methyl-pyridin-2-yl)-quinoline-2,6-diamine

The title compound, light brown solid, MS: m/e=371.2 (M+H$^+$); m.p. 134° C., was prepared in accordance with the general method of example 84 from (6-bromo-quinolin-2-yl)-(2-methoxy-benzyl)-amine (see example 2, step A) and commercially available 2-amino-6-methyl-pyridine.

Example 94

N2-(2-Methoxy-benzyl)-N6-(4-trifluoromethyl-pyrimidin-2-yl)-quinoline-2,6-diamine The title compound, light yellow solid, MS: m/e=426.1 (M+H$^+$); m.p. 114° C., was prepared in accordance with the general method of example 84 from (6-bromo-quinolin-2-yl)-(2-methoxy-benzyl)-amine (see example 2, step A) and commercially available 2-amino-4-trifluoromethyl-pyrimidine.

Example 95

N6-(2-tert-Butyl-2H-tetrazol-5-yl)-N2-(2-methoxy-benzyl)-quinoline-2,6-diamine

The title compound, light yellow solid, MS: m/e=404.5 (M+H$^+$); m.p. 156° C., was prepared in accordance with the general method of example 84 from (6-bromo-quinolin-2-yl)-(2-methoxy-benzyl)-amine (see example 2, step A) and commercially available 2-tert.-butyl-2H-tetrazole-5-yl-amine.

Example 96

N6-(5-Cyclopropyl-[1,3,4]oxadiazol-2-yl)-N2-(2-methoxy-benzyl)-quinoline-2,6-diamine The title compound, off-white solid, MS: m/e=388.4 (M+H$^+$); m.p. 199° C., was prepared in accordance with the general method of example 84 from (6-bromo-quinolin-2-yl)-(2-methoxy-benzyl)-amine (see example 2, step A) and commercially available 5-cyclopropyl-1,3,4-oxadiazole-2-yl-amine.

Example 97

N2-(2-Methoxy-benzyl)-N6-(5-trifluoromethyl-[1,3,4]oxadiazol-2-yl)-quinoline-2,6-diamine The title compound, off-white solid, MS: m/e=416.3 (M+H$^+$); m.p. 198° C., was prepared in accordance with the general method of example 84 from (6-bromo-quinolin-2-yl)-(2-methoxy-benzyl)-amine (see example 2, step A) and commercially available 5-trifluoromethyl-1,3,4-oxadiazole-2-yl-amine.

Example 98

N2-(2-Methoxy-benzyl)-N6-(4-trifluoromethyl-oxazol-2-yl)-quinoline-2,6-diamine

The title compound, light brown solid, MS: m/e=415.3 (M+H$^+$); m.p. 144° C., was prepared in accordance with the general method of example 84 from (6-bromo-quinolin-2-yl)-(2-methoxy-benzyl)-amine (see example 2, step A) and commercially available 4-trifluoromethyl-oxazole-2-yl-amine.

Example 99

N2-(2-Methoxy-benzyl)-N6-(5-trifluoromethyl-oxazol-2-yl)-quinoline-2,6-diamine

The title compound, light brown solid, MS: m/e=415.3 (M+H$^+$); m.p. 166° C., was prepared in accordance with the general method of example 84 from (6-bromo-quinolin-2-yl)-(2-methoxy-benzyl)-amine (see example 2, step A) and 5-trifluoromethyl-oxazol-2-yl-amine [CAS-No. 714972-00-6].

Example 100

N2-(2-Methoxy-benzyl)-N6-oxazol-2-yl-quinoline-2,6-diamine

The title compound, light yellow solid, MS: m/e=347.3 (M+H$^+$); m.p. 205° C., was prepared in accordance with the general method of example 84 from (6-bromo-quinolin-2-yl)-(2-methoxy-benzyl)-amine (see example 2, step A) and commercially available oxazole-2-yl-amine [CAS-No. 4570-45-0].

Example 101

N2-(2-Methoxy-benzyl)-N6-(6-trifluoromethyl-pyridin-2-yl)-quinoline-2,6-diamine

The title compound, off-white solid, MS: m/e=425.1 (M+H$^+$); m.p. 151° C., was prepared in accordance with the general method of example 84 from (6-bromo-quinolin-2-yl)-(2-methoxy-benzyl)-amine (see example 2, step A) and commercially available 2-amino-5-trifluoromethyl-pyridine.

Example 102

N2-(2-Methoxy-benzyl)-N6-(5-methyl-benzooxazol-2-yl)-quinoline-2,6-diamine

The title compound, off-white solid, MS: m/e=411.3 (M+H$^+$); m.p. 220° C., was prepared in accordance with the general method of example 84 from (6-bromo-quinolin-2-yl)-(2-methoxy-benzyl)-amine (see example 2, step A) and commercially available 5-methyl-benzoxazol-2-yl-amine [CAS-No. 64037-15-6].

Example 103

2-{3-[2-(2-Methoxy-benzylamino)-quinolin-6-ylamino]-phenyl}-ethanol

The title compound, yellow oil, MS: m/e=400.3 (M+H$^+$), was prepared in accordance with the general method of example 84 from (6-bromo-quinolin-2-yl)-(2-methoxy-benzyl)-amine (see example 2, step A) and commercially available 3-(2-hydroxyethyl)-aniline.

Example 104

N2-(2-Methoxy-benzyl)-N6-(3-piperidin-1-yl-[1,2,4]oxadiazol-5-yl)-quinoline-2,6-diamine The title compound, light brown foam, MS: m/e=431.3 (M+H$^+$), was prepared in accordance with the general method of example 84 from (6-bromo-quinolin-2-yl)-(2-methoxy-benzyl)-amine (see example 2, step A) and 3-(piperidin-1-yl)-[1,2,4]oxadiazol-5-yl-amine [CAS-No. 75565-19-4].

Example 105

$N^2$-(2,2-Dimethyl-2,3-dihydro-benzofuran-7-yl)-$N^6$-(6-methyl-pyridin-2-yl)-quinoline-2,6-diamine Step A (6-Bromo-quinolin-2-yl)-(2,2-dimethyl-2,3-dihydro-benzofuran-7-yl)-amine, orange oil, MS: m/e=371.2 (M+H$^+$), was prepared in accordance with the general method of example 2, step A, from 6-bromo-2 chloroquinoline and (2,2-dimethyl-2,3-dihydro-benzofuran-7-yl)-amine [CAS No. 68298-46-4].

Step B

The title compound, yellow foam, MS: m/e=397.2 (M+H$^+$), was prepared in accordance with the general method of example 84 from (6-bromo-quinolin-2-yl)-(2,2-dimethyl-2,3-dihydro-benzofuran-7-yl)-amine and commercially available 2-amino-6-methyl-pyridine.

The invention claimed is:

1. A compound of formula I

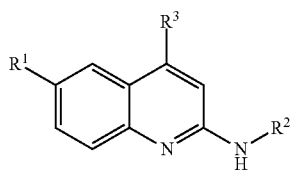

I wherein
$R^1$ is —NR$^a$—Ar$^1$, —NR$^b$CH$_2$—Ar$^1$, —CH$_2$NR$^b$—Ar$^1$, —NR$^c$C(O)—Ar$^1$, —OCH$_2$—Ar$^1$, —CH$_2$O—Ar$^1$, —CH$_2$CH$_2$—Ar$^1$, —CH=CH—Ar$^1$, —NHC(O)NH—Ar$^1$, —NHSO$_2$NH—Ar$^1$, —NR$^c$C(O)O—Ar$^1$, —C(O)NR$^c$CH$_2$—Ar$^1$, —CH$_2$NR$^b$CH$_2$—Ar$^1$, —NHC(=N—Ar$^1$)—Ar$^1$, —NR$^b$CH$_2$CH$_2$—Ar$^1$, or —NR$^b$CH$_2$CH$_2$O—Ar$^1$, $R^2$ is —Ar$^2$, —CHR$^d$—Ar$^2$, or —CH$_2$CH$_2$O—Ar$^2$, $R^3$ is hydrogen,
 phenyl, or pyridinyl, optionally substituted with one or more C$_{1-4}$-alkyl, halo, or C$_{1-4}$-alkoxy,
 —NR$^e$R$^f$, wherein R$^e$ and R$^f$ are each independently hydrogen, or
 —(CH$_2$)$_m$—OR$^g$, wherein m is from 2 to 6, Ar$^1$ and Ar$^2$ are each independently aryl or heteroaryl, each optionally substituted by one or more B, B is C$_{1-7}$-alkoxy,
 C$_{1-7}$-haloalkoxy,
 hydroxy,
 halo,
 C$_{1-7}$-alkyl, optionally substituted with one or more halo, hydroxy, or cyano,
 —S(O)$_2$—C$_{1-7}$-alkyl,
 —NR$^i$R$^{ii}$,
 —NR$^{iii}$S(O)$_2$R$^{iv}$,
 —NR$^{iii}$C(O)R$^v$,
 —C(O)NR$^{iii}$R$^{iv}$,
 —S(O)$_2$—NR$^{iii}$R$^{iv}$,
 —CH$_2$—O—R$^v$,
 —(OCH$_2$CH$_2$)$_n$—OR$^v$, wherein n is from 1 to 3,
 —CH$_2$—(OCH$_2$CH$_2$)$_n$—OR$^v$, wherein n is from 1 to 3,
 —C(O)R$^v$,
 cyano,
 nitro,
 allyl,
 C$_{3-7}$-cycloalkyl,
 5- to 7-membered monocyclic heterocycloalkyl, or
 two residues B in ortho-position to each other form a 3- to 4-membered bridge of the formula —CH$_2$CH$_2$CH$_2$—, —CH$_2$CH$_2$CH$_2$CH$_2$—, —O—C(R$^{vi}$)$_2$—O—, —OCH$_2$CH$_2$O—, —OCH(R$^{vii}$)CH(R$^{viii}$)—, R$^a$, R$^b$, R$^c$, R$^d$, and R$^g$ are each independently hydrogen or C$_{1-7}$-alkyl;

R$^i$, R$^{ii}$, R$^{iii}$, R$^{iv}$, and R$^v$ are each independently hydrogen, C$_{1-7}$-alkyl or —(CH$_2$)$_n$—C$_{3-7}$-cycloalkyl, wherein n is from 0 to 3;

R$^{vi}$, R$^{vii}$, and R$^{viii}$ are each independently hydrogen, C$_{1-4}$-alkyl or halogen;

or a pharmaceutically acceptable salt thereof.

2. The compound of claim 1, wherein
R$^1$ is —NR$^a$—Ar$^1$, —NR$^b$CH$_2$—Ar$^1$, —CH$_2$O—Ar$^1$, —CH$_2$CH$_2$—Ar$^1$, —CH=CH—Ar$^1$, —NHC(O)NH—Ar$^1$, —NHSO$_2$NH—Ar$^1$, or —NR$^c$C(O)O—Ar$^1$.

3. The compound of claim 2, wherein
R$^1$ is —NH—Ar$^1$, —NHCH$_2$—Ar$^1$, —CH$_2$O—Ar$^1$, —CH$_2$CH$_2$—Ar$^1$, —CH=CH—Ar$^1$, —NHSO$_2$NH—Ar$^1$, or —NR$^c$C(O)O—Ar$^1$.

4. The compound of claim 1, wherein
Ar$^1$ and Ar$^2$ are each independently phenyl, naphthyl, aromatic 5- or 6-membered monocyclic heteroaryl or aromatic 9- or 10-membered bicyclic heteroaryl, wherein the aromatic 5- or 6-membered monocyclic heteroaryl or aromatic 9- or 10-membered bicyclic heteroaryl each contain one, two, three or four heteroatoms selected from N, O and S, the remaining ring atoms being C, and wherein each Ar$^1$ and Ar$^2$ is optionally and independently substituted by one or more B.

5. The compound of claim 4, wherein
Ar$^1$ and Ar$^2$ are each independently selected from the group selected from the group consisting of phenyl, naphthyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, tetrazolyl, indolyl, benzofuranyl, benzothiophenyl, benzimidazolyl, benzoxyzolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phtalazinyl, or pteridinyl, each optionally substituted with one or more B.

6. The compound of claim 4, wherein
Ar$^1$ and Ar$^2$ are each independently selected from the group selected from the group consisting of phenyl, tetrazolyl, [1,3,4]-oxadiazolyl, [1,2,4]-oxadiazolyl, imidazolyl, oxazolyl, isoxazolyl, furanyl, pyridinyl, pyrimidinyl or benzoxazolyl, each optionally substituted with one of more B.

7. The compound of claim 1, wherein
R$^2$ is —CH$_2$—Ar$^2$ or —CH$_2$CH$_2$O—Ar$^2$.

8. The compound of claim 1, wherein R$^3$ is hydrogen.

9. The compound of claim 1 wherein B is selected from the group consisting of
C$_{1-7}$-alkoxy,
C$_{1-7}$-haloalkoxy,
halo, $C_{1-7}$-alkyl, optionally substituted with one or more halo, or hydroxy,
—CH$_2$—O—R$^v$,
—(OCH$_2$CH$_2$)$_n$—OR$^v$, wherein n is from 1 to 3,
—CH$_2$—(OCH$_2$CH$_2$)$_n$—OR$^v$, wherein n is from 1 to 3,
$C_{3-7}$-cycloalkyl,
5- to 7-membered monocyclic heterocycloalkyl, preferably piperidinyl, and
two residues B in ortho-position to each other forming a —O—C(R$^{vi}$)$_2$—O— bridge;
wherein R$^v$ is as defined above, preferably R$^v$ is methyl;
and wherein R$^{vi}$ is as defined above, preferably R$^{vi}$ is hydrogen.

10. The compound of claim 9, wherein B is selected from the group consisting of
$C_{1-7}$-alkoxy,
$C_{1-7}$-haloalkoxy,
halo,
$C_{1-7}$-alkyl, optionally substituted with one or more halo, or hydroxy,
—CH$_2$—O—R$^v$,
—(OCH$_2$CH$_2$)$_n$—OR$^v$, wherein n is from 1 to 3,
—CH$_2$—(OCH$_2$CH$_2$)$_n$—OR$^v$, wherein n is from 1 to 3,
$C_{3-7}$-cycloalkyl, and
piperidinyl;
wherein R$^v$ is as defined above, preferably R$^v$ is methyl.

11. The compound of claim 9, wherein B is selected from the group consisting of
$C_{1-7}$-alkoxy,
halo,
$C_{1-7}$-alkyl, optionally substituted with one or more halo, and
two residues B in ortho-position to each other forming a —O—C(R$^{vi}$)$_2$—O— bridge,
wherein R$^{vi}$ is as defined above, and preferably is hydrogen.

12. The compound of claim 1, selected from the group consisting of
N2-(2-phenoxy-ethyl)-N6-pyridin-3-ylmethyl-quinoline-2,6-diamine,
N2-(2-methoxy-benzyl)-N6-pyridin-3-ylmethyl-quinoline-2,6-diamine,
N6-benzyl-N2-(2-methoxy-benzyl)-quinoline-2,6-diamine,
N6-(2-methoxy-benzyl)-N2-(2-phenoxy-ethyl)-quinoline-2,6-diamine,
N6-(3-methoxy-benzyl)-N2-(2-phenoxy-ethyl)-quinoline-2,6-diamine,
N2-(2-methoxy-benzyl)-4-phenyl-N6-pyridin-3-ylmethyl-quinoline-2,6-diamine,
N2,N6-bis-(2-methoxy-benzyl)-quinoline-2,6-diamine,
N6-(3-methoxy-benzyl)-N2-(2-methoxy-benzyl)-quinoline-2,6-diamine,
N2-(2-methoxy-benzyl)-N6-(2-trifluoromethoxy-benzyl)-quinoline-2,6-diamine,
N6-(3-methoxy-benzyl)-N2-(2-methoxy-benzyl)-4-phenyl-quinoline-2,6-diamine, and
N2,N6-bis-(2-methoxy-benzyl)-4-phenyl-quinoline-2,6-diamine.

13. The compound of claim 1, selected from the group consisting of
N2-(5-methyl-furan-2-ylmethyl)-N6-pyridin-3-ylmethyl-quinoline-2,6-diamine,
N6-(2-methoxy-benzyl)-N2-(5-methyl-furan-2-ylmethyl)-quinoline-2,6-diamine,
N6-(3-methoxy-benzyl)-N2-(5-methyl-furan-2-ylmethyl)-quinoline-2,6-diamine,
N6-benzyl-N2-(5-methyl-furan-2-ylmethyl)-quinoline-2,6-diamine,
N-2-(4-fluoro-2-methoxy-benzyl)-4-phenyl-N-6-pyridin-3-ylmethyl-quinoline-2,6-diamine,
N2-(2-methoxy-benzyl)-N6-pyridin-3-ylmethyl-4-o-tolyl-quinoline-2,6-diamine,
N-2-(2-methoxy-benzyl)-4-(3-methoxy-phenyl)-N-6-pyridin-3-ylmethyl-quinoline-2,6-diamine,
4-(2,5-difluoro-phenyl)-N2-(2-methoxy-benzyl)-N6-pyridin-3-ylmethyl-quinoline-2,6-diamine,
N-6-benzyl-N-2-(4-fluoro-2-methoxy-benzyl)-4-phenyl-quinoline-2,6-diamine,
N-2-(4-fluoro-2-methoxy-benzyl)-4-phenyl-N-6-&-pyridin-4-ylmethyl-quinoline-2,6-diamine, and
N-6-2-benzyl-N-2-(4-fluoro-2-methoxy-benzyl)-4-o-tolyl-quinoline-2,6-diamine.

14. The compound of claim 1, selected from the group consisting of
N6-benzyl-N2-(4-fluoro-2-methoxy-benzyl)-quinoline-2,4,6-triamine,
N6-benzyl-N2-(2-methoxy-benzyl)-quinoline-2,4,6-triamine,
N2-(2-methoxy-benzyl)-N6-pyridin-3-ylmethyl-quinoline-2,4,6-triamine,
N2-(5-methyl-furan-2-ylmethyl)-N6-pyridin-3-ylmethyl-quinoline-2,4,6-triamine,
N6-benzyl-N2-(5-methyl-furan-2-ylmethyl)-quinoline-2,4,6-triamine,
N2-(3-methoxy-benzyl)-N6-pyridin-3-ylmethyl-quinoline-2,6-diamine,
N6-benzyl-N2-(5-fluoro-2-methoxy-benzyl)-quinoline-2,4,6-triamine,
N2-(5-fluoro-2-methoxy-benzyl)-N6-pyridin-3-ylmethyl-quinoline-2,4,6-triamine,
N2-benzo[1,3]dioxol-4-ylmethyl-N6-pyridin-3-ylmethyl-quinoline-2,6-diamine,
1-[2-(2-methoxy-benzylamino)-quinolin-6-yl]-3-(4-methoxy-phenyl)-urea, and
N-(4-fluorophenyl)-N'-{2-[(2-methoxybenzyl)amino]quinolin-6-yl}sulfamide.

15. The compound of claim 1, selected from the group consisting of
N6-(2-ethyl-2H-tetrazol-5-yl)-N2-(2-methoxy-benzyl)-quinoline-2,6-diamine,
N2-(2-methoxy-benzyl)-N6-(5-methyl-isoxazol-3-yl)-quinoline-2,6-diamine,
N2-(2-methoxy-benzyl)-N6-(4-methyl-pyrimidin-2-yl)-quinoline-2,6-diamine,
N2-(2-methoxy-benzyl)-N6-pyridin-2-yl-quinoline-2,6-diamine,
N2-(2-methoxy-benzyl)-N6-(4-trifluoromethyl-pyrimidin-2-yl)-quinoline-2,6-diamine,
N6-(5-cyclopropyl-[1,3,4]oxadiazol-2-yl)-N2-(2-methoxy-benzyl)-quinoline-2,6-diamine,
N2-(2-methoxy-benzyl)-N6-(6-trifluoromethyl-pyridin-2-yl)-quinoline-2,6-diamine,
2-{3-[2-(2-methoxy-benzylamino)-quinolin-6-ylamino]-phenyl}-ethanol, and
N2-(2,2-dimethyl-2,3-dihydro-benzofuran-7-yl)-N$^6$-(6-methyl-pyridin-2-yl)-quinoline-2,6-diamine.

16. The compound of claim 1, wherein
R$^1$ is —NR$^a$—Ar$^1$, —NR$^b$CH$_2$—Ar$^1$, —CH$_2$O—Ar$^1$, —CH$_2$CH$_2$—Ar$^1$, —CH═CH—Ar$^1$, —NHC(O)NH—Ar$^1$, —NHSO$_2$NH—Ar$^1$, or —NR$^c$C(O)O—Ar$^1$.

$R^2$ is —$Ar^2$, —$CH_2$—$Ar^2$, or —$CH_2CH_2O$—$Ar^2$,
$R^3$ is hydrogen, or
  phenyl or pyridinyl, optionally substituted with one or more $C_{1-4}$-alkyl, halo, or $C_{1-4}$-alkoxy,
$Ar^1$ and $Ar^2$ are each independently phenyl, naphthyl, aromatic 5- or 6-membered monocyclic heteroaryl or aromatic 9- or 10-membered bicyclic heteroaryl, wherein each heteroaryl contains one, two, three or four heteroatoms selected from N, O and S, the remaining ring atoms being C, each $Ar^1$ and $Ar^2$ is optionally and independently substituted by one or more B,
B is $C_{1-7}$-alkoxy,
  $C_{1-7}$-haloalkoxy,
  hydroxy,
  halo,
  $C_{1-7}$-alkyl, optionally substituted with one or more halo, hydroxy, or cyano,
  —$S(O)_2$—$C_{1-7}$-alkyl,
  —$NR^iR^{ii}$,
  —$NR^{iii}S(O)_2R^{iv}$,
  —$NR^{iii}C(O)R^{iv}$,
  —$C(O)NR^{iii}R^{iv}$,
  —$S(O)_2$—$NR^{iii}R^{iv}$,
  —$CH_2$—O—$R^v$,
  —$(OCH_2CH_2)_n$—$OR^v$, wherein n is from 1 to 3,
  —$CH_2$—$(OCH_2CH_2)_n$—$OR^v$, wherein n is from 1 to 3,
  —$C(O)R^v$,
  cyano,
  nitro,
  allyl,
  $C_{3-7}$-cycloalkyl,
  5- to 7-membered monocyclic heterocycloalkyl, or
  two residues B in ortho-position to each other form a 3- to 4-membered bridge of the formula —$CH_2CH_2CH_2$—, —$CH_2CH_2CH_2CH_2$—, —O—C$(R^{vi})_2$—O—, —$OCH_2CH_2O$—, —$OCH(R^{vii})CH(R^{viii})$—,
$R^a$, $R^b$, $R^c$, and $R^g$ are each independently hydrogen or $C_{1-7}$-alkyl;
$R^i$, $R^{ii}$, $R^{iii}$, $R^{iv}$, and $R^v$ are each independently hydrogen, $C_{1-7}$-alkyl or —$(CH_2)_n$—$C_{3-7}$-cycloalkyl, wherein n is from 0 to 3;
$R^{vi}$, $R^{vii}$, and $R^{viii}$ are each independently hydrogen, $C_{1-4}$-alkyl or halogen;
or a pharmaceutically acceptable salt thereof.

17. A pharmaceutical composition comprising a therapeutically effective amount of a compound of formula I

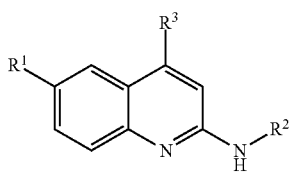

I wherein
$R^1$ is —$NR^a$, —$Ar^1$, —$NR^bCH_2$—$Ar^1$, —$CH_2NR^b$—$Ar^1$, —$NR^cC(O)$—$Ar^1$, —$OCH_2$—$Ar^1$, —$CH_2O$—$Ar^1$, —$CH_2CH_2$—$Ar^1$, —CH=CH—$Ar^1$, —NHC(O)NH—$Ar^1$, —$NHSO_2NH$—$Ar^1$, —$NR^cC(O)O$—$Ar^1$, —C(O)$NR^cCH_2$—$Ar^1$, —$CH_2NR^bCH_2$—$Ar^1$, —NHC(=N—$Ar^1$)—$Ar^1$, —$NR^bCH_2CH_2CH_2$—$Ar^1$, or —$NR^bCH_2CH_2O$—$Ar^1$,
$R^2$ is —$Ar^2$, —$CHR^d$—$Ar^2$, or —$CH_2CH_2O$—$Ar^2$,
$R^3$ is hydrogen,
  phenyl, or pyridinyl, optionally substituted with one or more $C_{1-4}$-alkyl, halo, or $C_{1-4}$-alkoxy,
  —$NR^eR^f$, wherein $R^e$ and $R^f$ are each independently hydrogen, or
  —$(CH_2)_m$—$OR^g$, wherein m is from 2 to 6,
$Ar^1$ and $Ar^2$ are each independently aryl or heteroaryl, each optionally substituted by one or more B,
B is $C_{1-7}$-alkoxy,
  $C_{1-7}$-haloalkoxy,
  hydroxy,
  halo,
  $C_{1-7}$-alkyl, optionally substituted with one or more halo, hydroxy, or cyano,
  —$S(O)_2$—$C_{1-7}$-alkyl,
  —$NR^iR^{ii}$,
  —$NR^{iii}S(O)_2R^{iv}$,
  —$NR^{iii}C(O)R^{iv}$,
  —$C(O)NR^{iii}R^{iv}$,
  —$S(O)_2$—$NR^{iii}R^{iv}$,
  —$CH_2$—O—$R^v$,
  —$(OCH_2CH_2)_n$—$OR^v$, wherein n is from 1 to 3,
  —$CH_2$—$(OCH_2CH_2)_n$—$OR^v$, wherein n is from 1 to 3,
  —$C(O)R^v$,
  cyano,
  nitro,
  allyl,
  $C_{3-7}$-cycloalkyl,
  5- to 7-membered monocyclic heterocycloalkyl, or
  two residues B in ortho-position to each other form a 3- to 4-membered bridge of the formula —$CH_2CH_2CH_2$—, —$CH_2CH_2CH_2CH_2$—, —O—C$(R^{vi})_2$—O—, —$OCH_2CH_2O$—, —$OCH(R^{vii})CH(R^{viii})$—,
$R^a$, $R^b$, $R^c$, $R^d$, and $R^g$ are each independently hydrogen or $C_{1-7}$-alkyl;
$R^i$, $R^{ii}$, $R^{iii}$, $R^{iv}$, and $R^v$ are each independently hydrogen, $C_{1-7}$-alkyl or —$(CH_2)_n$—$C_{3-7}$-cycloalkyl, wherein n is from 0 to 3;
$R^{vi}$, $R^{vii}$, and $R^{viii}$ are each independently hydrogen, $C_{1-4}$-alkyl or halogen;
or a pharmaceutically acceptable salt thereof and a pharmaceutically acceptable carrier.

* * * * *